United States Patent
Blau

(10) Patent No.: US 10,839,633 B2
(45) Date of Patent: *Nov. 17, 2020

(54) SYSTEMS AND METHODS FOR DETECTING FAKE OR ALTERED BULLION, COINS, AND METAL

(71) Applicant: Sigma Metalytics LLC, Chico, CA (US)

(72) Inventor: David Arthur Blau, Chico, CA (US)

(73) Assignee: SIGMA METALYTICS LLC, Chico, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/545,461

(22) Filed: Aug. 20, 2019

(65) Prior Publication Data
US 2019/0371107 A1    Dec. 5, 2019

Related U.S. Application Data

(63) Continuation of application No. 15/409,106, filed on Jan. 18, 2017, now Pat. No. 10,417,855.
(Continued)

(51) Int. Cl.
*G07D 5/08* (2006.01)
*G06Q 30/00* (2012.01)
(Continued)

(52) U.S. Cl.
CPC .............. *G07D 5/08* (2013.01); *G01N 27/041* (2013.01); *G01N 33/20* (2013.01); *G06Q 30/018* (2013.01); *G06Q 30/0185* (2013.01); *G07D 5/04* (2013.01)

(58) Field of Classification Search
CPC .. G07D 5/08; G07D 5/06; G07D 5/04; G07D 5/02; G07D 5/005; G07D 5/00;
(Continued)

(56) References Cited

U.S. PATENT DOCUMENTS

| 3,992,938 A | 11/1976 | Miller |
| 4,226,323 A | 10/1980 | Dautremont |

(Continued)

FOREIGN PATENT DOCUMENTS

| CA | 2479146 A1 | 3/2005 |
| GB | 2287341 A | 9/1995 |

(Continued)

OTHER PUBLICATIONS

"SigmaCheck Fully Featured Eddy Current Conductivity Meter," Retrieved from the Internet: URL: http://www.ethernde.com/instruments/conductivity-meters/sigmacheck (retrieved Mar. 28, 2017).
(Continued)

*Primary Examiner* — Toan M Le
(74) *Attorney, Agent, or Firm* — Venable LLP; Henry J. Daley

(57) ABSTRACT

A system for verifying authenticity of precious metal coins and bars includes a sensor system defining a sample region configured to receive a precious metal coin or bar therein; a sample support; and a data processor configured to communicate with the sensor system so as to receive a detection signal therefrom and to provide an output signal. The system includes a data storage device and an output display. The sensor system detects a bulk electrical property of the coin or bar. The data processor processes the detection signal and retrieves a stored physical property from the data storage device to provide an output signal that includes at least a measured value of the bulk electrical property and a corresponding range of expected values. The output display uses the output signal to display information for a user to be able to make an authenticity verification of the coin or bar.

20 Claims, 14 Drawing Sheets

Related U.S. Application Data

(60) Provisional application No. 62/280,028, filed on Jan. 18, 2016.

(51) Int. Cl.
*G01N 27/04* (2006.01)
*G01N 33/20* (2019.01)
*G07D 5/04* (2006.01)

(58) Field of Classification Search
CPC .. G06Q 30/0185; G06Q 30/018; G01N 33/20; G01N 27/041
See application file for complete search history.

(56) References Cited

U.S. PATENT DOCUMENTS

| | | |
|---|---|---|
| 4,797,614 A | 1/1989 | Nelson |
| 4,971,187 A | 11/1990 | Furuya et al. |
| 5,213,190 A | 5/1993 | Furneaux et al. |
| 5,525,903 A | 6/1996 | Mandl et al. |
| 5,552,704 A | 9/1996 | Mallory et al. |
| 7,584,833 B2 | 9/2009 | Howells |
| 10,417,855 B2 * | 9/2019 | Blau ............... G01N 27/041 |
| 2005/0051409 A1 | 3/2005 | Howells |
| 2006/0151284 A1 | 7/2006 | Howells |
| 2009/0107800 A1 | 4/2009 | Nishida et al. |
| 2010/0261421 A1 | 10/2010 | Wendell et al. |
| 2013/0315437 A1 | 11/2013 | Kerschner et al. |

FOREIGN PATENT DOCUMENTS

| | | |
|---|---|---|
| JP | 2000-163621 A | 6/2000 |
| KR | 1019890015176 A | 10/1998 |
| WO | 93/21608 A1 | 10/1993 |

OTHER PUBLICATIONS

Carlosena et al. "Sensing in Coin Discriminators." Feb. 6-8, 2007, SAS 2007—IEEE Sensors Applications Symposium, San Diego, CA 6 pages.

International Search Report and Written Opinion issued in PCT Application No. PCT/US2014/055239 dated Dec. 10, 2014.

* cited by examiner

SYSTEMS AND METHODS FOR DETECTING FAKE OR ALTERED BULLION, COINS, AND METAL

This application is a continuation of U.S. application Ser. No. 15/409,106 filed Jan. 18, 2017, now U.S. Pat. No. 10,417,855, which claims priority to U.S. Provisional Application No. 62/280,028 filed Jan. 18, 2016, the entire content of which is hereby incorporated by reference.

BACKGROUND

1. Technical Field

The field of the currently claimed embodiments of this invention relates to devices and methods for verifying the authenticity of precious metal coins and bars.

2. Discussion of Related Art

Precious metal coins and bullion are valued by their metal content. By altering the metal, or by inserting a different metal into a coin or bar, a fake or altered bar or coin can be made to look, feel, and weigh the same as a real one. Even testing the surface of the coin or bar does not guarantee that the inside is actually made of the correct material.

No single method of precious metal sample determination can guarantee that the sample is what it is supposed to be. Existing methods are slow, messy, and expensive, and some are destructive. For example, melting can be used, but obviously this destroys the precious metal sample and is very expensive.

Therefore, there remains a need for a detection device that is accurate, fast, portable, and non-destructive.

SUMMARY

According to some embodiments of the present invention, a system for verifying authenticity of precious metal coins and bars includes a sensor system defining a sample region configured to receive at least one of a precious metal coin or a precious metal bar therein. The system includes a sample support arranged to support the at least one of the precious metal coin or the precious metal bar in the sample region. The system includes a data processor configured to communicate with the sensor system so as to receive a detection signal therefrom and to provide an output signal. The system includes a data storage device configured to communicate with the data processor, the data storage device storing at least some physical properties corresponding to a precious metal of interest. The system also includes an output display configured to communicate with the data processor to receive the output signal and to display information based on the output signal. The sensor system detects at least one of a bulk electrical property of the at least one of the precious metal coin or the precious metal bar. The data processor is configured to process the detection signal from the sensor system and to retrieve a stored physical property corresponding to a precious metal from the data storage device to provide the output signal such that the output signal includes at least a measured value of the bulk electrical property and a corresponding range of expected values of the bulk electrical property. The output display uses the output signal to display information based on the measured value of the bulk electrical property and the corresponding range of expected values of the bulk electrical property for a user to be able to make an authenticity verification of the precious metal coin or the precious metal bar.

According to some embodiments of the present invention, a system for verifying authenticity of precious metal coins and bars includes a sensor system defining a sample region configured to receive at least one of a precious metal coin or a precious metal bar therein. The system includes a sample support arranged to support the at least one of the precious metal coin or the precious metal bar in the sample region. The system includes a data processor configured to communicate with the sensor system so as to receive a detection signal therefrom and to provide an output signal. The system includes a data storage device configured to communicate with the data processor, the data storage device storing at least some physical properties corresponding to a precious metal of interest. The system also includes an output display configured to communicate with the data processor to receive the output signal and to display information based on the output signal. The sensor system detects a surface property of first and second sides of the precious metal coin or the precious metal bar. The data processor is configured to process the detection signal from the sensor system to provide the output signal such that the output signal includes at least a measured value of a thickness value of the precious metal coin or the precious metal bar. The output display uses the output signal to display information based on the thickness value of the precious metal coin or the precious metal bar for a user to be able to make an authenticity verification of the precious metal coin or the precious metal bar.

According to some embodiments of the invention, a method for verifying authenticity of precious metal coins and bars using an electronic apparatus includes inputting into the electronic apparatus information identifying at least a type of a precious metal coin or a precious metal bar to be verified. The method includes performing a measurement of a bulk electrical property of the precious metal coin or the precious metal bar using the electronic apparatus. The method includes retrieving a stored bulk electrical property of the precious metal coin or the precious metal bar corresponding to the measured bulk electrical property for the inputted type of the precious metal coin or the precious metal bar. The method includes providing information from the electronic apparatus for verification of authenticity of the precious metal coin or the precious metal bar based on the measured bulk electrical property and the retrieved bulk electrical property.

BRIEF DESCRIPTION OF THE DRAWINGS

Further objectives and advantages will become apparent from a consideration of the description, drawings, and examples.

DETAILED DESCRIPTION

Figure 1A:
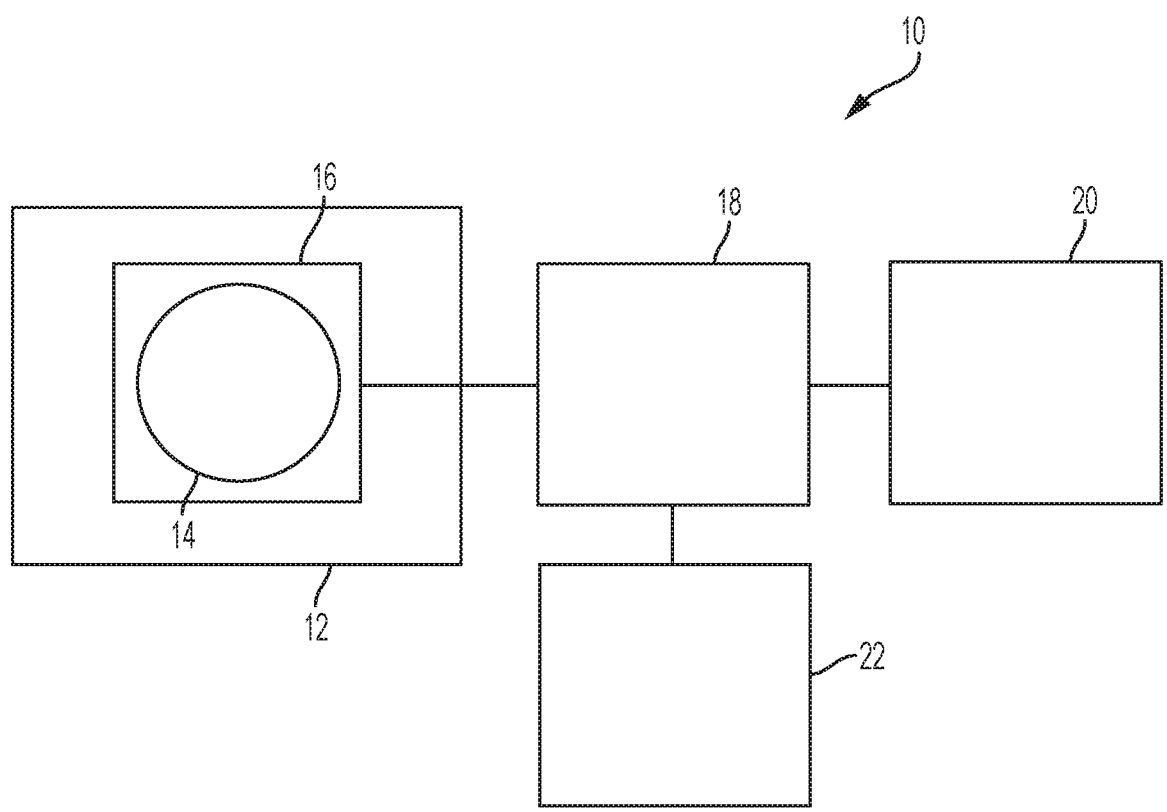
FIG. 1A is a first schematic drawing of a precious metal verification system according to some embodiments of the present invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Precious metal coins and bullion are valued by their metal content. The term "bullion" refers to precious metal objects such as bars, coins, and/or rounds that are valued in terms of their metal content. The term "coins" is intended to include numismatic coins and bullion coins in which numismatic coins have value as a coin either as money and/or as a collectable item and bullion coins have value based primarily upon the metal content with a small premium. A precious metal "round" can be considered to be a type of coin in a general sense, as will be intended herein. By altering the metal, or by inserting a different metal into a coin or bar, a fake or altered bar or coin can be made to look, feel, and weigh the same as a real one. Even testing the surface of the coin or bar does not guarantee that the inside of the bar is actually the correct material. The device and methods disclosed herein allow a user to look all the way through a bar or coin and determine whether the metal is the correct metal or alloy.

By measuring the thickness of the sample in two different ways, in combination with knowing the alloy or element, and the alloy or element's resistivity, the resistivity through the entire sample is validated. Also, knowing the thickness and the weight in combination with the area of the coin or bullion gives the specific gravity, which for a given alloy sample is also known. If the resistivity through the bulk is correct, and the specific gravity is correct, then the metal element or alloy must be the one represented by the coin or bullion.

The claimed invention differs from what currently exists. Using x-ray backscatter, the surface of a precious metal (PM) sample can be measured for elemental composition. However, only the surface is measured (typically 10 microinches deep), so plating can fool this method. Ultrasound can be used to find discontinuities in the bulk of a PM sample, but the method requires a mechanical thickness measurement, and index matching fluids. Specific gravity can be measured by immersion in a fluid bath, but this method is messy.

None of these methods alone constitutes a certain measurement that the PM is correct and consistent through the bulk, so multiple measurements are required for assurance. The systems and methods described herein can verify the authenticity of the PM sample through its bulk using electrical measurements, and no liquids are required.

The systems and methods according to some embodiments measure the thickness of the sample, which is not an easy dimension to measure, and allow the user to measure the diameter (in the case of coins) or the length and width (in the case of bars) and easily determine the specific gravity without immersion in a liquid bath. In combination with the bulk resistivity, the PM sample is validated completely. The process is fast and the system is easy to use. The systems and methods do not modify the sample, and completely check the material through the bulk. They also work on thin and thick samples.

A system for verifying authenticity of precious metal coins and bars is represented schematically in FIG. 1A. The system 10 includes a sensor system 12 defining a sample region 14 configured to receive at least one of a precious metal coin or a precious metal bar therein. The system 10 further includes a sample support 16 arranged to support the at least one of the precious metal coin or the precious metal bar in the sample region 14. The system 10 includes a data processor 18 configured to communicate with the sensor system 12 so as to receive a detection signal therefrom and to provide an output signal. The system 10 includes a data storage device 20 configured to communicate with the data processor 18, the data storage device 20 storing at least some physical properties corresponding to a precious metal of interest. The system 10 also includes an output display 22 configured to communicate with the data processor 18 to receive the output signal and to display information based on the output signal. The sensor system 12 detects at least one of a bulk electrical property of the at least one of the precious metal coin or the precious metal bar. The data processor 18 is configured to process the detection signal from the sensor system 12 and to retrieve a stored physical property corresponding to a precious metal from the data storage device 20 to provide the output signal such that the output signal includes at least a measured value of the bulk electrical property and a corresponding range of expected values of the bulk electrical property. The output display 22 uses the output signal to display information based on the measured value of the bulk electrical property and the corresponding range of expected values of the bulk electrical property for a user to be able to make an authenticity verification of the precious metal coin or the precious metal bar.

According to some embodiments of the invention, the sensor system 12 further detects a surface electrical property of the at least one of the precious metal coin or the precious metal bar. The data processor 18 is further configured to process the detection signal from the sensor system 12 and to retrieve a stored physical property corresponding to a precious metal from the data storage device 20 to provide the output signal such that the output signal includes at least the measured value of surface electrical property and a corresponding range of expected values of the surface electrical property. The output display 22 uses the output signal to display information based on the measured value of the surface electrical property and the corresponding range of expected values of the surface electrical property for a user to be able to make an authenticity verification of the precious metal coin or the precious metal bar.

According to some embodiments of the invention, the system 10 further includes a user input system configured to communicate with the data storage device 20 and the data processor 18. The user input system allows a user to select at least one of a precious metal type, alloy parameters, weight, or shape.

According to some embodiments of the invention, the sensor system 12 further detects a surface property of first and second sides of the precious metal coin or the precious metal bar. The data processor 18 is configured to process the detection signal from the sensor system 12 to provide the output signal such that the output signal includes at least a measured value of a thickness value of the precious metal coin or the precious metal bar. The output display 22 uses the output signal to display information based on the thickness value of the precious metal coin or the precious metal bar for a user to be able to make an authenticity verification of the precious metal coin or the precious metal bar.

According to some embodiments of the invention, the data processor 18 is further configured to retrieve a specific gravity corresponding to a precious metal from the data storage device 20 and receive a weight value corresponding to the precious metal coin or the precious metal bar, and to provide the output signal such that the output signal further includes an expected diameter of the precious metal coin or an expected area of the precious metal bar. The information based on the thickness value is the expected diameter of the precious metal coin or an expected length and width of the precious metal bar.

Figure 1B:
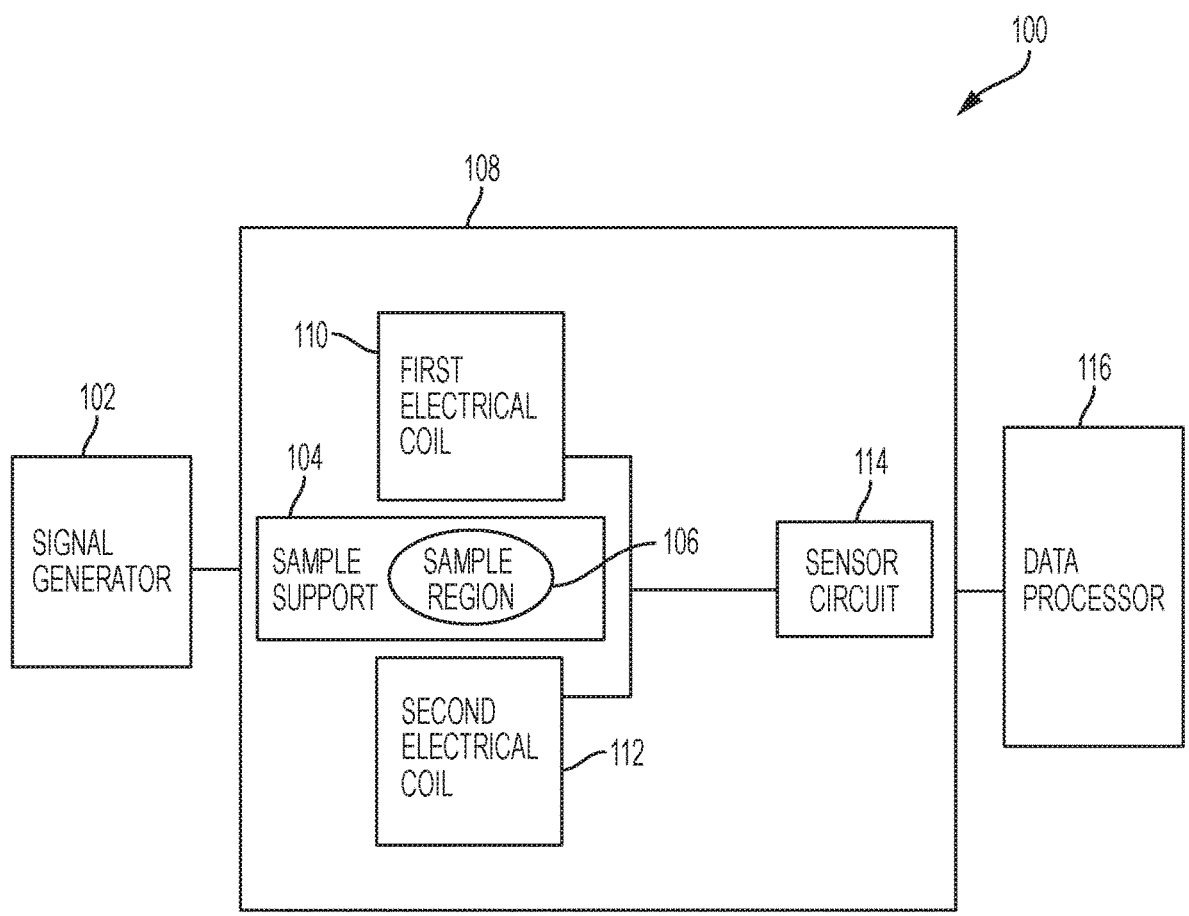
FIG. 1B is a second schematic drawing of a precious metal verification system according to some additional embodiments of the present invention.

A system for verifying authenticity of precious metal coins and bars is represented schematically in FIG. 1B. The system 100 includes a signal generator 102, and a sample support 104 arranged proximate the signal generator 102, the sample support 104 having a sample region 106 to support at least one of a precious metal coin or a precious metal bar. The system 100 also includes a sensor system 108. The sensor system 108 includes first and second electrical coils 110, 112 spaced apart with the sample region 106 therebetween. The first and second electrical coils 110, 112 are spaced apart sufficiently widely to accommodate the precious metal coin or the precious metal bar therebetween. The sensor system 108 also includes a sensor circuit 114 selectively connecting the signal generator 102 to the first and second electrical coils 110, 112. The sensor circuit 114 is configured to provide a measurement of a current in the first electrical coil 110 and a measurement of a voltage induced in the second electrical coil 112.

The system 100 also includes a data processor 116. The data processor 116 is configured to communicate with the sensor system 108 so as to receive the measurement of the current through the first electrical coil 110 and the measurement of the voltage induced in the second electrical coil 112. The data processor 116 is configured to receive a surface resistivity value corresponding to the precious metal coin or the precious metal bar. The data processor 116 is also configured to receive a thickness value of the precious metal coin or the precious metal bar. The data processor 116 is configured to calculate a bulk property of the precious metal coin or the precious metal bar based on the measurement of the current and the measurement of the voltage. The data processor 116 is configured to compare the bulk property to a test property based on the surface resistivity value and the thickness value to determine one of agreement or disagreement therewith, and provide information concerning verification of authenticity of the precious metal coin or the precious metal bar based on the agreement or disagreement between the bulk property and the test property.

While the example above uses the measurement of the current through the first electrical coil 110 and the measurement of the voltage induced in the second electrical coil 112 to calculate a bulk property of the precious metal coin or the precious metal bar, an alternative would be to measure or control the voltage for the first electrical coil 110 and estimate the current drive based on impedance, and to measure the current in the second electrical coil 112 and estimate the magnetic flux from this current and the impedance.

According to some embodiments of the invention, the data processor 116 is configured to calculate the bulk property based on a phase shift between the measurement of the current and the measurement of the voltage. According to some embodiments, the bulk property is a bulk resistivity of the precious metal coin or the precious metal bar.

According to some embodiments of the invention, the data processor 116 is configured to control the signal generator 102 to adjust a frequency of a voltage applied to the first electrical coil 110 such that a phase shift between the measurement of the current and the measurement of the voltage has a predetermined value. The data processor 116 is configured to calculate the bulk property of the precious metal coin or the precious metal bar based on the frequency at which the phase shift has the predetermined value and the indication of the thickness value of the precious metal coin or the precious metal bar. According to some embodiments, the predetermined value of the phase shift is 45 degrees.

Figure 1C:
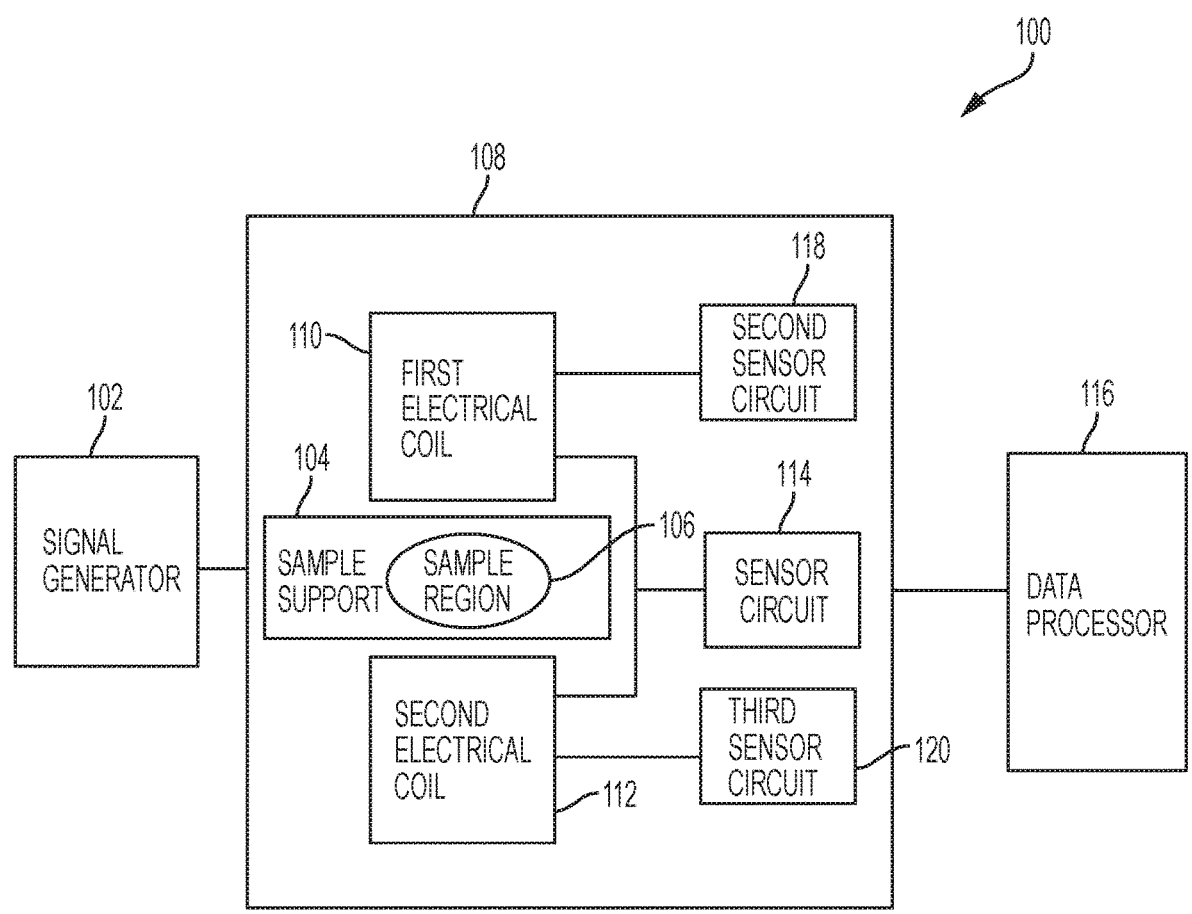
FIG. 1C is a third schematic drawing of a precious metal verification system according to some additional embodiments of the present invention.

A system for verifying authenticity of precious metal coins and bars according to some embodiments is represented schematically in FIG. 1C, wherein like reference numerals as in FIG. 1B correspond to like features. In addition to the features described with reference to FIG. 1B, the system 100 according to some embodiments includes a sensor system 108 that further includes a second sensor circuit 118 selectively connecting the signal generator 102 to the first electrical coil 110 to provide a second measurement of a current in the first electrical coil 110. The data processor 116 is configured to communicate with the sensor system 108 so as to receive the second measurement of the current through the first electrical coil 110. The data processor 116 is configured to calculate the surface resistivity value of the precious metal coin or the precious metal bar based on the second measurement of the current through the first electrical coil 110. The data processor 116 is configured to compare the bulk property to a test property based on the calculated surface resistivity value and the thickness value to determine one of agreement or disagreement therewith, and provide information concerning verification of authenticity of the precious metal coin or the precious metal bar based on the agreement or disagreement between the bulk property and the test property.

According to some embodiments of the invention, the sensor system 108 further includes a third sensor circuit 120 selectively connecting the signal generator 102 to the second electrical coil 112 to provide a measurement of a current in the second electrical coil 112. The data processor 116 is configured to communicate with the sensor system 108 so as to receive the measurement of the current through the second electrical coil 112. The data processor 116 is configured to calculate the thickness value based on the second measurement of the current through the first electrical coil and the measurement of the current through the second electrical coil. The data processor 116 is configured to provide information concerning verification of authenticity of the precious metal coin or the precious metal bar based on the calculated thickness value.

Figure 2:
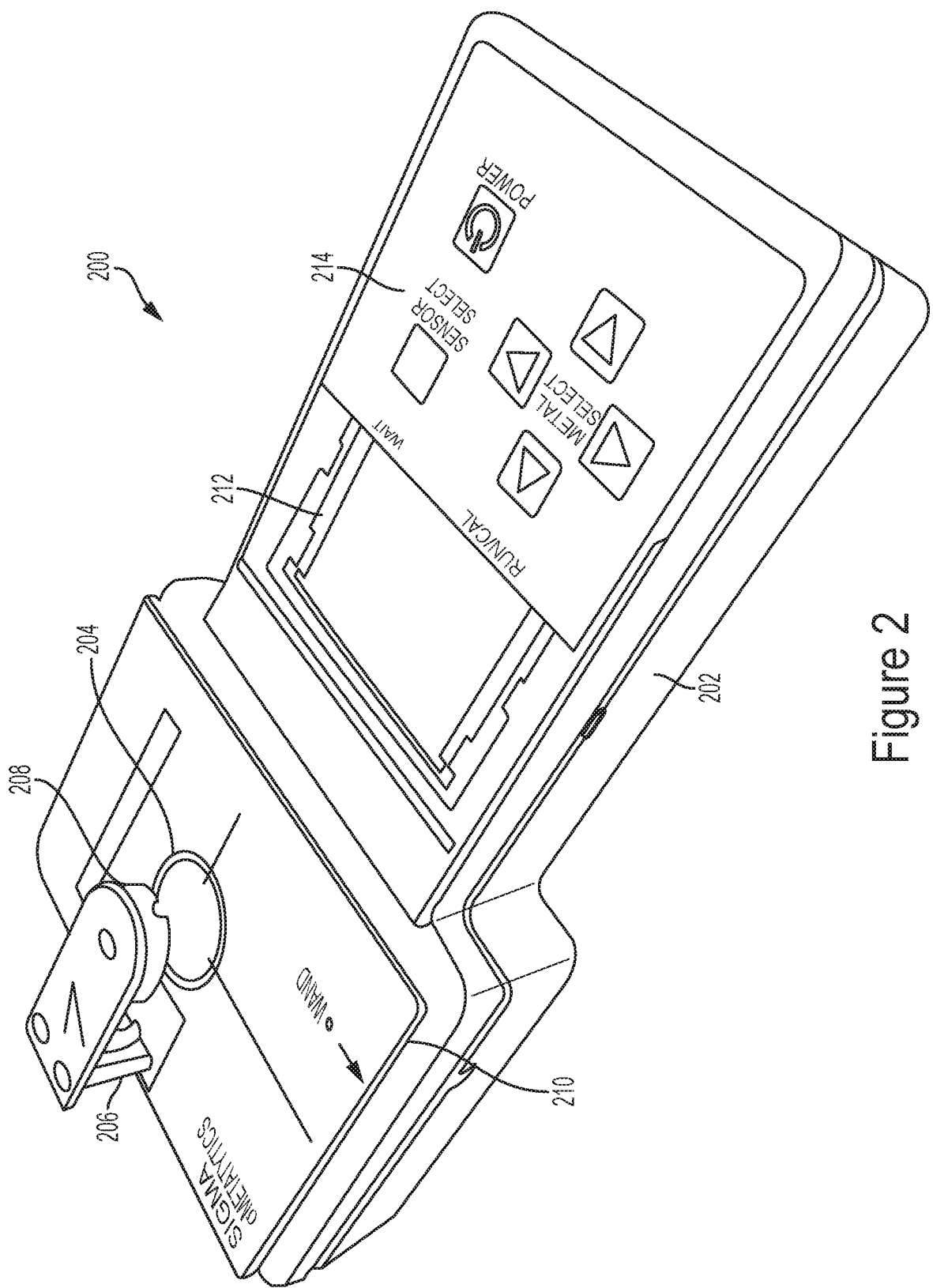
FIG. 2 shows the outside of the device according to some embodiments and generally illustrates how different features are related.

According to some embodiments of the invention, the system further includes a user interface in communication with the data processor. The user interface may include an input device and a display device. An example of an input device includes a keypad that includes one or more touch-sensitive or depressible buttons. However, the broad concepts of the current invention are not limited to only this example. The display device may be a visual display, such as a display screen or a light source, for example. The display device may also include an audio device that provides voice commands, beeps, or other sounds that enable the system to communicate with a user. The input device and output device may be combined in a touch-sensitive display. According to some embodiments, the system can include multiple input devices and display devices. An example input device and display device is shown in FIG. 2, described below.

According to some embodiments of the invention, the user interface is configured to receive an indication from a user of an expected composition of precious metal coin or the precious metal bar. The data processor according to some embodiments is configured to receive the surface resistivity value corresponding to the precious metal coin or the precious metal bar from a database based on the indication of the expected composition received from the user. According to some embodiments, the user interface is configured to receive from a user the thickness value of the precious metal coin or the precious metal bar.

According to some embodiments of the invention, the user interface is configured to display information concerning verification of authenticity of the precious metal coin or the precious metal bar. According to some embodiments of the invention, the user interface is configured to display one of an expected length, width, or diameter of the sample via the display device. According to some embodiments, the user interface is configured to display a non-numerical indication of information concerning verification of authenticity of the precious metal coin or the precious metal bar. According to some embodiments, the user is configured to display an indication of a difference between an expected value of the precious metal coin or the precious metal bar and a value determined using the sensor system. The display may show a margin of error for an expected value, and may indicate whether the determined value falls within the margin. The display may indicate an acceptable margin by displaying a green region, and indicating whether the determined value falls within the green region. The display may use other colors, for example, yellow and red, to indicate margins of error that are questionable or are too high for the sample to be valid. If the determined value falls within the red region, for example, the sample is likely inauthentic.

According to some embodiments of the invention, the system 100 includes a second sensor circuit 118 selectively connecting the signal generator 102 to the first electrical coil 110, the second sensor circuit being configured to provide a second measurement of a current in the first electrical coil 110. The system 100 also includes a third sensor circuit 120 selectively connecting the signal generator 102 to the second electrical coil 112, the third sensor circuit 120 being configured to provide a measurement of a current in the second electrical coil 112. The data processor 116 is configured to communicate with the sensor system 108 so as to receive the second measurement of the current through the first electrical coil 110 and the measurement of the current through the second electrical coil 112, receive a specific gravity value corresponding to the precious metal coin or the precious metal bar, and receive a weight value of the precious metal coin or the precious metal bar. The data processor 116 is configured to calculate a thickness value of the precious metal coin or the precious metal bar based on the second measurement of the current in the first electrical coil and the measurement of the current in the second electrical coil, and calculate a value of a length or a diameter of the precious metal coin or the precious metal bar based on the specific gravity value, the weight value, and the calculated thickness.

According to some embodiments of the invention, the data processor 116 is further configured to determine a first distance between the first electrical coil 110 and the precious metal coin or the precious metal bar based on the second measurement of the current through the first electrical coil 110. The data processor 116 is further configured to determine a second distance between the second electrical coil 112 and the precious metal coin or the precious metal bar based on the measurement of the current through the second electrical coil 112. The data processor 116 is configured to determine the thickness value of the precious metal coin or the precious metal bar based on the first distance, the second distance, and a pre-determined distanced between the first electrical coil 110 and the second electrical coil 112.

According to some embodiments of the invention, the data processor 116 is configured to calculate an expected area of the sample based on the thickness, the specific gravity value, and the weight value. The user interface is configured to provide a non-numerical indication of the expected area and an acceptable error range to allow a user to compare the expected area to an actual area of the precious metal coin or the precious metal bar.

According to some embodiments of the invention, the user interface is configured to indicate first and second reference lines for positioning first and second edges of the precious metal bar. The user interface is also configured to indicate third and fourth reference lines indicating expected positions of third and fourth edges of the precious metal bar based on the expected area. The user interface is configured to receive input from a user adjusting a position of one of the third and fourth reference lines to correspond to one of the third and fourth edges of the precious metal bar. The user interface is configured to adjust the other of the third and fourth reference lines to indicate the expected position of the other of the third and fourth edges of the precious metal bar based on the expected area, and indicate an acceptable error range to allow a user to compare the expected area of the precious metal bar to an actual area of the precious metal bar.

According to some embodiments of the invention, the system includes a weight measurement component in communication with the data processor. The data processor is configured to receive the weight value of the precious metal coin or the precious metal bar from the weight measurement component.

Figure 1D:
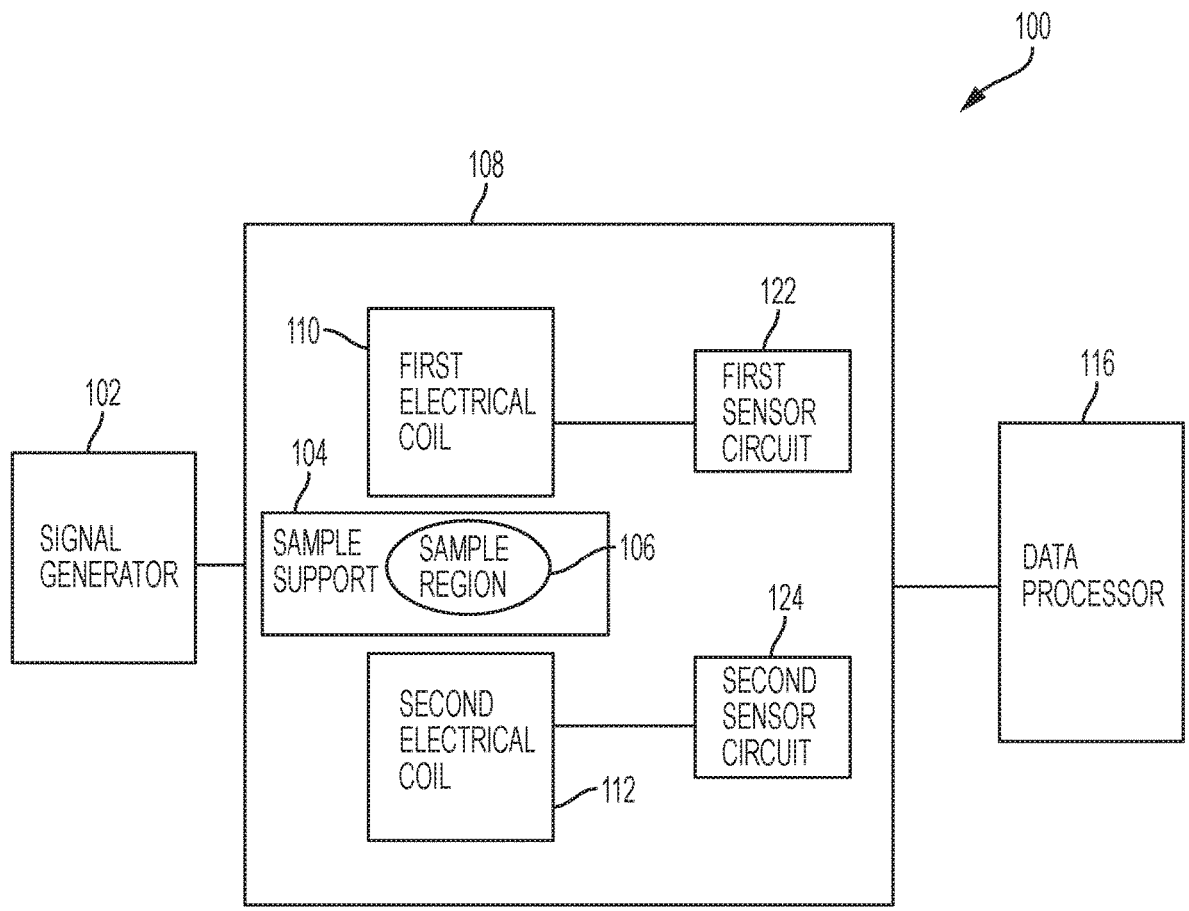
FIG. 1D is a fourth schematic drawing of a precious metal verification system according to some additional embodiments of the present invention.

A system 100 for verifying authenticity of precious metal coins and bars according to some embodiments is shown in FIG. 1D, wherein like reference numerals as in FIG. 1B indicate like features. The system 100 includes a signal generator 102, and a sample support 104 arranged proximate the signal generator 102. The sample support 104 has a sample region 106 to support at least one of a precious metal coin or a precious metal bar. The system 100 includes a sensor system 108 including first and second electrical coils 110, 112 spaced apart with the sample region 106 therebetween. The first and second electrical coils 110, 112 are spaced apart sufficiently widely to accommodate the precious metal coin or the precious metal bar therebetween. The sensor system 108 includes a first sensor circuit 122 selectively connecting the signal generator 102 to the first electrical coil 110. The first sensor circuit 122 is configured to provide a measurement of a current in the first electrical coil 110. The sensor system 108 includes a second sensor circuit 124 selectively connecting the signal generator 102 to the second electrical coil 112, the second sensor circuit 124 being configured to provide a measurement of a current in the second electrical coil 112. The system 100 includes a data processor 116 configured to communicate with the sensor system 108 so as to receive the measurement of the current through the first electrical coil 110 and the measurement of the current through the second electrical coil 112. The data processor 116 is configured to receive a specific gravity value corresponding to the precious metal coin or the precious metal bar, and receive a weight value of the precious metal coin or the precious metal bar. The data processor 116 is configured to calculate a thickness value of the precious metal coin or the precious metal bar based on the measurement of the current in the first electrical coil and the measurement of the current in the second electrical coil. The data processor 116 is configured to calculate a value of a length or a diameter of the precious metal coin or the precious metal bar based on the specific gravity value, the weight value, and the calculated thickness.

According to some embodiments, the data processor 116 is further configured to determine a first distance between the first electrical coil and the precious metal coin or the precious metal bar based on the measurement of the current through the first electrical coil. The data processor 116 is further configured to determine a second distance between the second electrical coil and the precious metal coin or the precious metal bar based on the measurement of the current through the second electrical coil. The data processor 116 is further configured to determine the thickness value of the precious metal coin or the precious metal bar based on the first distance, the second distance, and a pre-determined distanced between the first electrical coil and the second electrical coil.

The system according to the embodiments of the invention may also be referred to herein as a "detection system" or "detection device." The signal generator may also be referred to herein as a "sine wave generator."

According to some embodiments of the invention, a method for verifying authenticity of precious metal coins and bars includes inputting into the electronic apparatus information identifying at least a type of a precious metal coin or a precious metal bar to be verified. The method further includes performing a measurement of a bulk electrical property of the precious metal coin or the precious metal bar using the electronic apparatus. The method includes retrieving a stored bulk electrical property of the precious metal coin or the precious metal bar corresponding to the measured bulk electrical property for the inputted type of the precious metal coin or the precious metal bar. The method also includes providing information from the electronic apparatus for verification of authenticity of the precious metal coin or the precious metal bar based on the measurement of the bulk electrical property and the stored bulk electrical property.

According to some embodiments of the invention, the method further includes performing a measurement of a surface electrical property of the precious metal coin or the precious metal bar using the electronic apparatus. The method further includes retrieving a stored surface electrical property of the precious metal coin or the precious metal bar corresponding to the measured surface electrical property for the inputted type of the precious metal coin or the precious metal bar. The method also includes providing information from the electronic apparatus for verification of authenticity of the precious metal coin or the precious metal bar based on the measurement of the surface electrical property and the stored surface electrical property.

According to some embodiments of the invention, the method further includes performing a measurement of a surface electrical property of first and second sides of the precious metal coin or the precious metal bar using the electronic apparatus. The method includes calculating a thickness of the sample based on the surface electrical property of the first and second sides of the precious metal coin or the precious metal bar using the electronic apparatus. The method further includes providing information from the electronic apparatus for verification of authenticity of the precious metal coin or the precious metal bar based on the measurement of the thickness of the precious metal coin or the precious metal bar.

According to some embodiments of the invention, a method for verifying authenticity of precious metal coins and bars includes receiving a surface resistivity value corresponding to the precious metal coin or the precious metal bar, and receiving a thickness value of the precious metal coin or the precious metal bar. The method further includes performing a measurement through a bulk of the precious metal coin or the precious metal bar, and calculating a bulk property of the precious metal coin or the precious metal bar based on the measurement. The method further includes comparing the bulk property to a test property based on the surface resistivity value and the thickness value to determine one of agreement or disagreement therewith, and providing information concerning verification of authenticity of the precious metal coin or the precious metal bar based on the agreement or disagreement between the bulk property and the test property.

The term bulk electrical property is intended to be an electrical property that involves more than a surface electrical property of a precious metal coin or precious metal bar. For example, the bulk electrical property can be, but is not limited to, electric resistance that would occur for a current passing from one point on the surface of the precious metal coin or precious metal bar, to another point on a different surface of the precious metal coin or precious metal bar. For example, the resistance for a current to flow from a point on the obverse of the precious metal coin to a point on the reverse of the precious metal coin. Similarly, top surface and bottom surface for a precious metal bar, etc.

A surface electrical property is, for example, an electrical resistivity of a precious metal coin or precious metal bar down to some depth generally referred to as the "skin depth" in the electrical arts. The skin depth can be roughly a millimeter to a few or several millimeters, for example.

According to some embodiments, the bulk property is a bulk resistivity of the precious metal coin or the precious metal bar. According to some embodiments, providing information concerning verification of authenticity of the precious metal coin or the precious metal bar comprises displaying the information concerning verification via a non-numerical display.

A detection system according to some embodiments of the invention is shown in FIG. 2. The detection system 200 includes a housing 202 that houses many of the components, including the first electrical coil. The housing 202 also acts as a sample support that supports the sample. The target area 204 indicates the target position of the sample over the first electrical coil. The detection system 200 also includes a support 206 that supports the second electrical coil 208 such that it is spaced apart from the first electrical coil by a known distance.

The detection system 200 according to some embodiments includes a weight measurement component 210 that is integrated into the platform on which the sample is placed. The weight measurement component 210 may determine the weight of the sample and may communicate the weight to the data processor for verifying the authenticity of the sample.

As shown in FIG. 2, the detection system 200 according to some embodiments includes a display device 212 and an input device 214. The display device may also be referred to herein as an "output display." The input device 214 may be a keypad or other data entry means. The input device may also be referred to herein as a "user input system."

Figure 3:
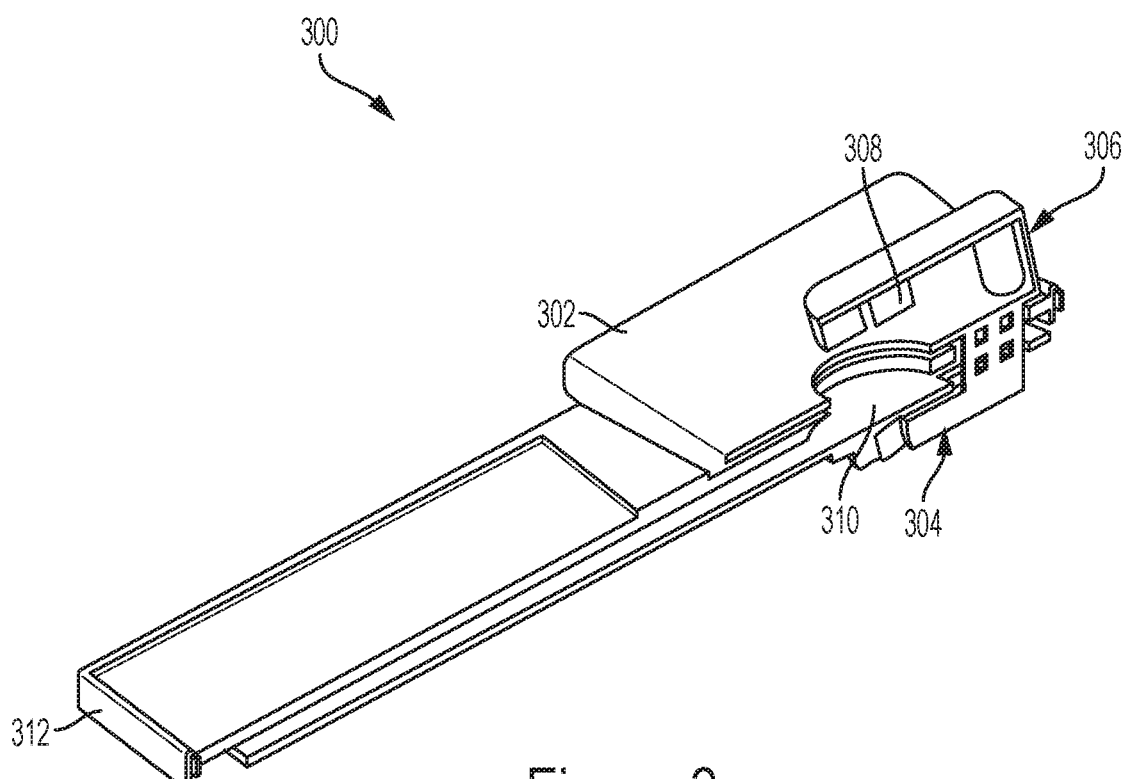
FIG. 3 shows a cross-section of the device illustrating how the weight sensor supports the first electrical coil, and where the support structure for the second electrical coil is located.

FIG. 3 shows a cross-section of the detection system 200 shown in FIG. 2. The detection system 300 includes a weight sensor platform 302 and a weight sensor load cell 304. The detection system 300 also includes the support 306 supporting the second electrical coil 308. The support 306 is connected to the weight cell to maintain constant distance between the second electrical coil 308 and the first electrical coil. The space 310 for the first electrical coil to be disposed inside the housing 312 is also shown.

Figure 6:
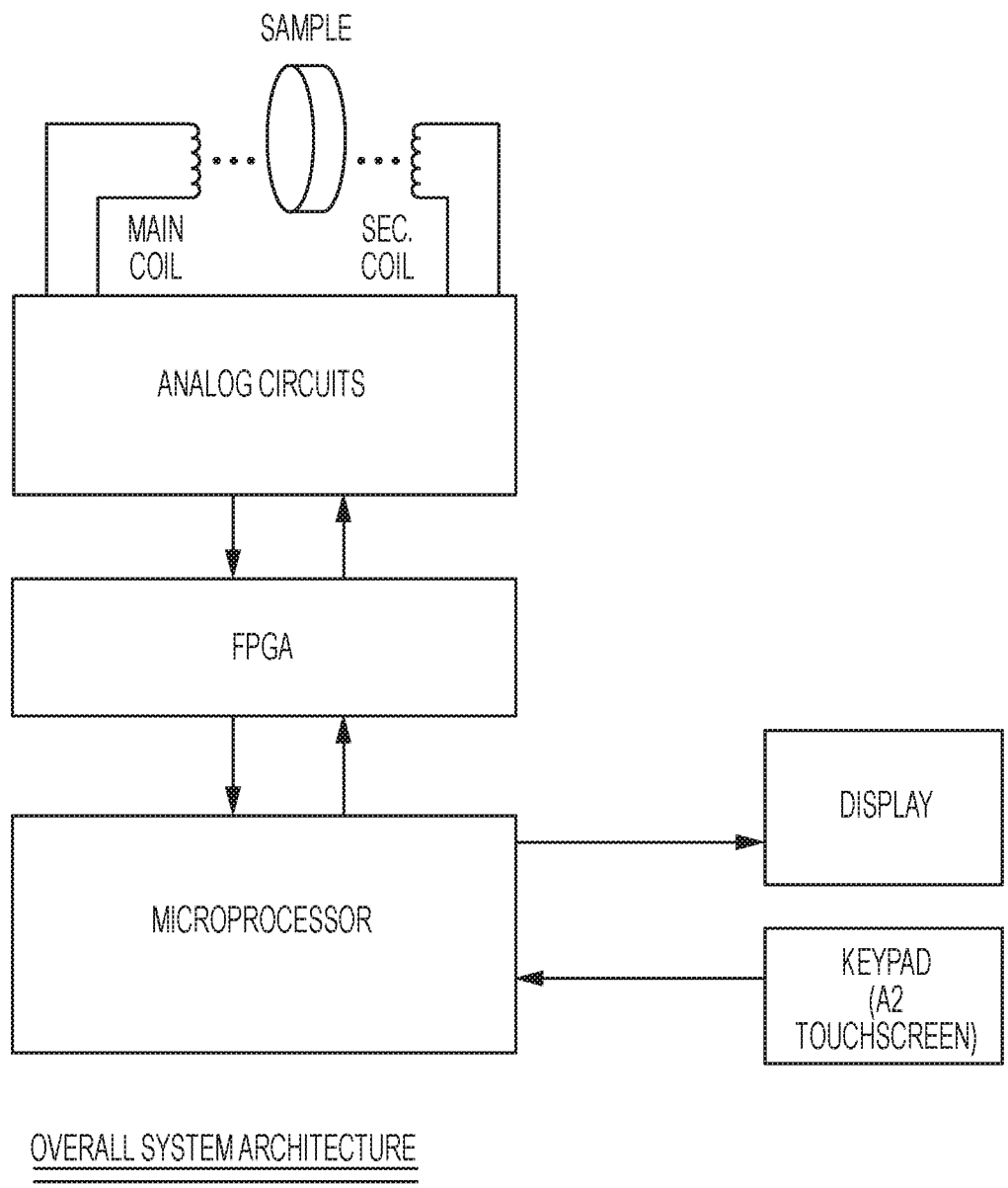
FIG. 6 shows the overall circuit plan according to some embodiments.
Figure 7:
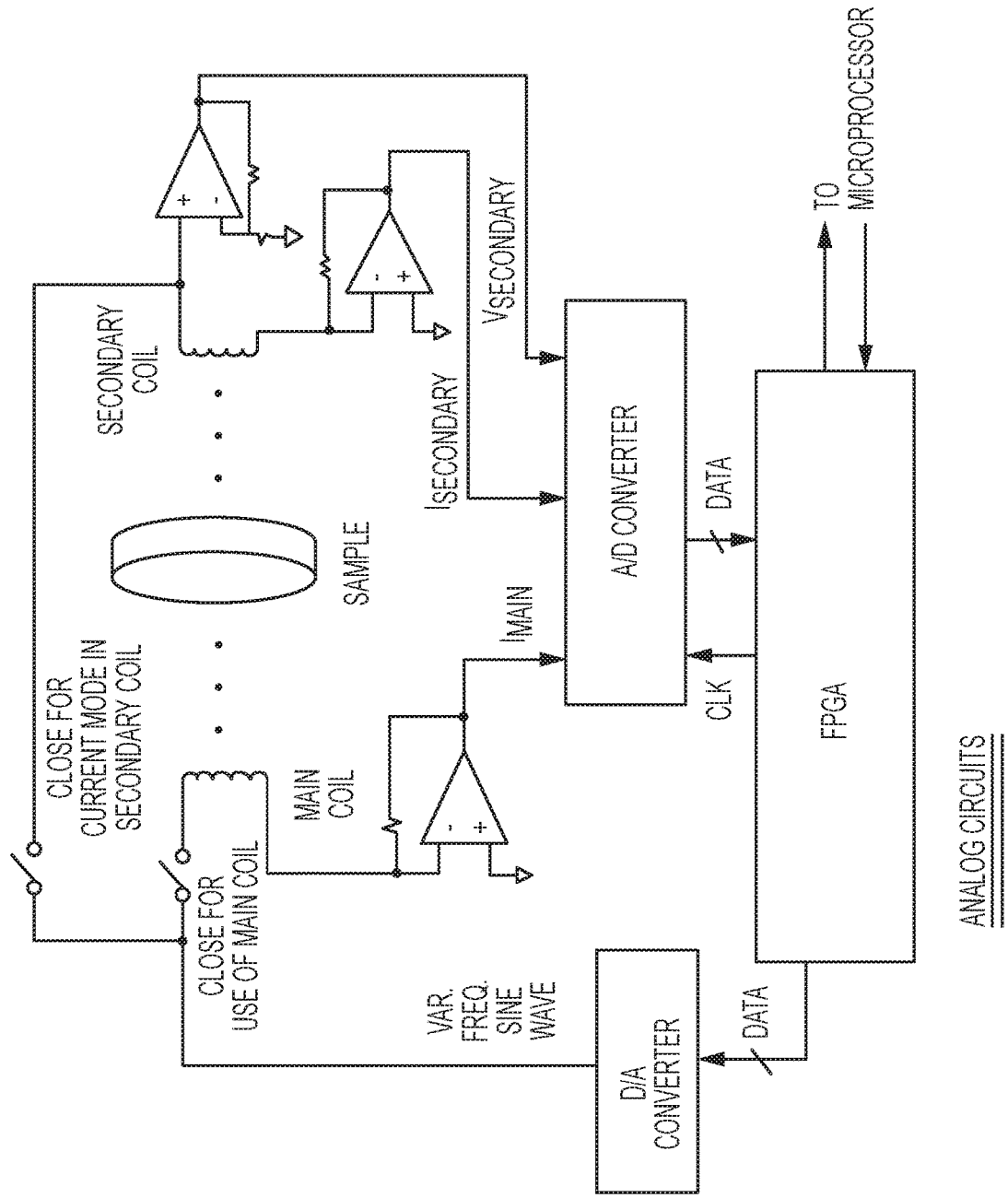
FIG. 7 shows details of the analog circuit topology according to some embodiments.

A number of components are disposed inside the housing 312. These can include multiple frequency sine wave generators, a synchronous detector, an analog-to-digital converter, and a data processor such as a microprocessor or computer, for example. FIG. 6 shows an overview of the system architecture, and FIG. 7 shows the analog circuits in more detail. The analog-to-digital converter and the synchronous detector may form at least part of the sensor system 108 shown in FIGS. 1B-1D. The sine wave generators may provide a known alternating current or a known alternating voltage. The data processor can be a dedicated "hard-wired" device, or it can be a programmable device. The data processor may be in communication with a memory or data storage device. The memory may store a program to be executed by the data processor for determining the authenticity of the sample. The memory can also store a metal database with specific gravity and resistivity information, as well as other types of information for a given metal or type of sample. The information in the metal database may be directed to a variety of different metals, and/or may be specific to known types of coin and bullion.

According to some embodiments of the invention, the detection device includes an adjustable support that separates the first coil from the second coil by a distance that can be adjusted. For example, when measuring large bars, the first and second coils must be separated sufficiently far apart that the bar can fit between them. However, because the electrical signal diminishes as the 4th power of the distance between the coil, it can be beneficial to separate the two coils by the minimum amount necessary to place the sample between them. Thus, an adjustable support can be used to separate the coils by a desirable distance. The adjustable support may have an encoder, for example, a linear encoder, that provides a high-sensitivity measurement of the distance between the two coils. This distance can also be obtained during a calibration process, but having an encoder monitor the separation distance can eliminate the need for determining the separation distance by calibration. The two coils and adjustable support may be electrically connected but physically separated from the rest of the device, for example, by having wires that connect the coils and adjustable support to the device. The two coils and adjustable support can then be easily manipulated and positioned to measure a large bar, without having to move or manipulate the bar.

The detection device may also include a scale or length measuring aid. For example, measurement lines similar to those on a ruler may be printed on the upper surface of the platform on which the sample is placed. A user may use the lines to determine the length, width, or diameter of a sample. The user may then enter this information into the input device, and the data processor may use the input information to determine the validity of the sample.

Alternatively, the data processor may display an expected sample length, width, or diameter, and the user may use the length measurement to confirm that the sample has the expected dimensions. If the sample does not have the expected dimensions, this may be an indication that the sample is not valid. According to some embodiments, the data processor may calculate an expected area of the sample, and then the user interface may indicate an expected length to which the user can compare the actual sample.

Figure 4A:
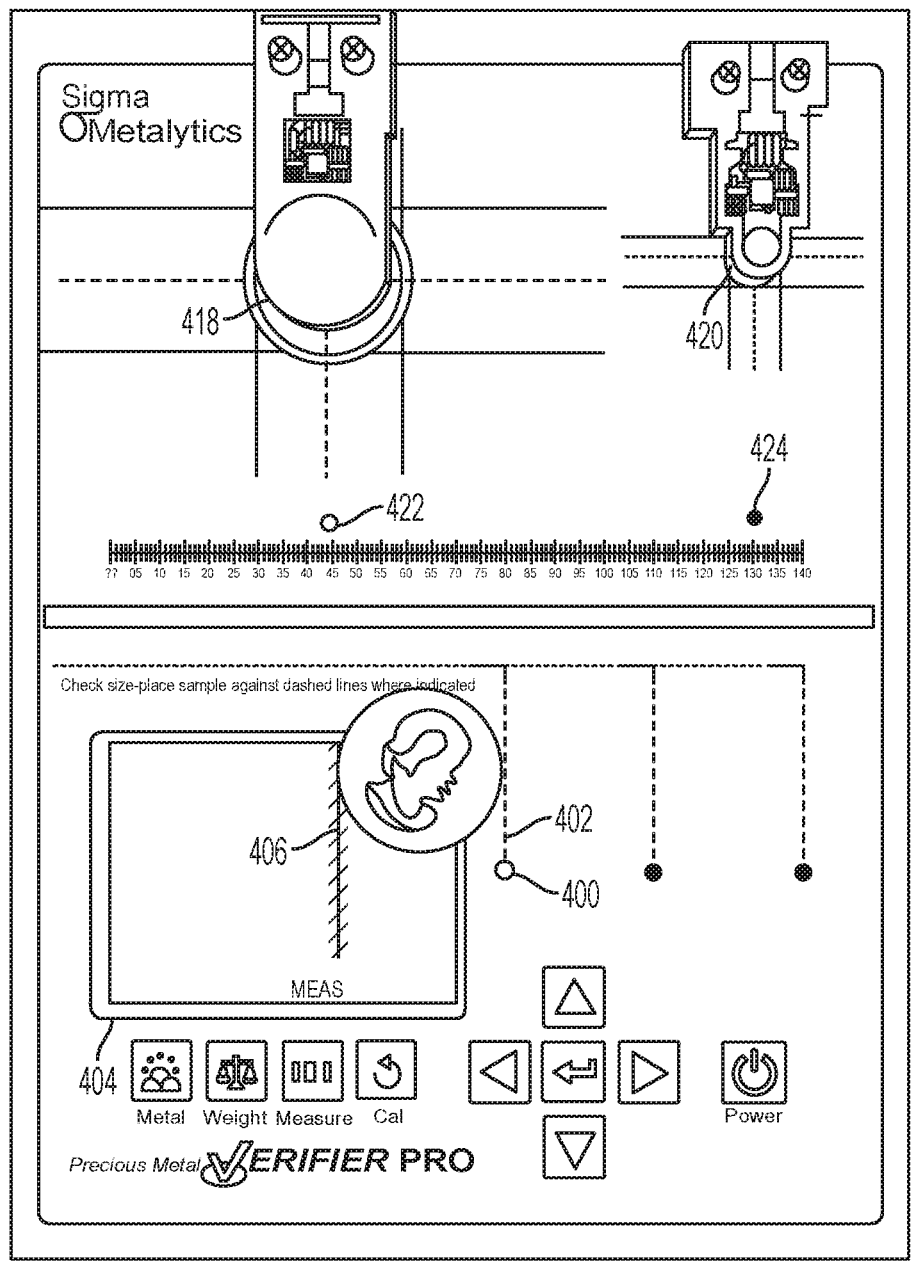
FIG. 4A illustrates a user interface for comparing an expected diameter of a sample to the actual diameter of the sample.

FIG. 4A shows an embodiment in which the user interface indicates the expected diameter of the sample. An indicator light 400 indicates a first line 402. A display screen 404 indicates a second line 406, as well as a shaded region on either side of the second line 406. The user aligns one edge of the coin with the first line 402, and the opposite edge of the coin with the second line 406. If the second edge falls within the shaded region surrounding the second line 406, then coin is determined to have the expected area.

Figure 4B:
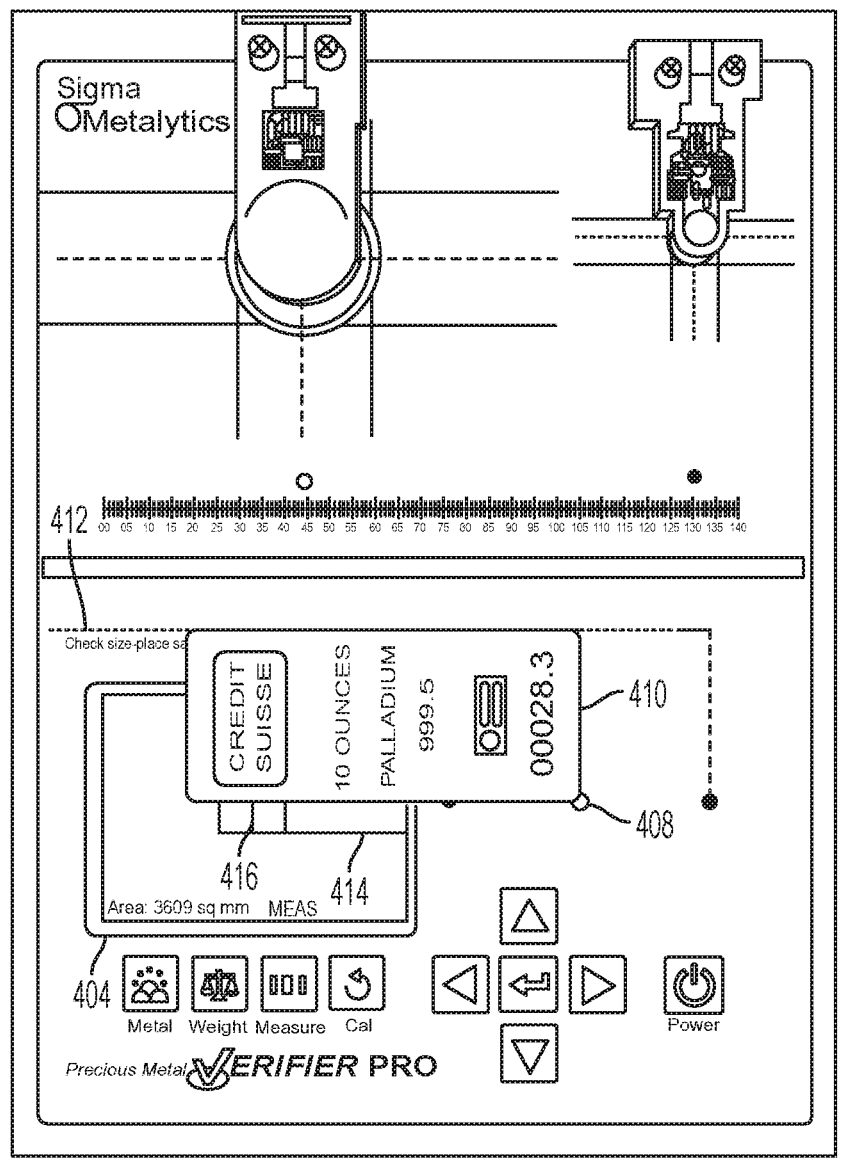
FIG. 4B illustrates a user interface for comparing an expected area of a sample to the actual area of the sample.

FIG. 4B shows an embodiment in which the user interface indicates the expected length and width of the sample. An indicator light 408 indicates a first line 410. The data processor then calculates expected positions of third and fourth edges of the sample based on the assumption that a first edge of the sample is aligned with the first line 410, and a second edge of the sample is aligned with a second line 412. The display device 404 shows a third line 414 and a fourth line 416 that correspond to the expected area. The user aligns first and second edges of the sample with the first and second lines 410, 412. The user then uses the user interface to adjust the position of the third line 414 or the fourth line 416. For example, the user may adjust the third line 414 to correspond to the position of the third edge of the sample. In the example shown in FIG. 4B, the user moves the third line 414 upwards, and the motion of the third line 414 is reflected on the display device. As third line 414 moves upwards, the data processor calculates a new position of the fourth line 416 that corresponds to the expected area, and the display device 404 updates the position of the fourth line 416. In the example shown in FIG. 4B, as the user moves the third line 414 upwards, the fourth line 416 moves to the left. The user continues adjusting the position of the third line until it corresponds to the third edge of the sample. The user then examines the fourth edge of the sample to determine whether it is above the fourth line, or falls within the acceptable margin of error indicated by the shaded regions on either side of the fourth line 416. If the fourth edge does not fall within the shaded region, then the sample is not authentic.

According to some embodiments, a user controls the detection device using the data processor, the display device, and the input device. The user enters the expected metal or sample by looking it up in a metal database. The metal database may be saved in the memory, and a portion of the entries in the metal database may be displayed on the display device. The user may use the input device to scroll through the metal database and select a metal or sample.

The user can then weigh the sample and enter the weight using the input device, or can use the built-in weight sensor, which may be in communication with the data processor. The user then places the sample on the target area. In FIG. 2, the target area 204 is indicated by a circle. The sample may be placed on top of this circle. The data processor is connected to the AC power supply in such a way as it can specify the frequency and amplitude of the output signal. The output signal may be a sine wave, for example.

Reference is now made to FIG. 1C. The signal generated by the signal generator 102 is applied to the first electrical coil 110, and the current through the first electrical coil 110 is measured using the second sensor circuit 118. The sensor system 108 may include an analog-to-digital converter. The second electrical coil 112 is supported such that it faces the first electrical coil 110, and such that the two electrical coils 110, 112 are separated by a known distance.

While the first electrical coil 110 may be shown and referred to herein as being position below the second electrical coil 112, the embodiments of the invention are not limited to this configured. According to some embodiments, the first electrical coil 110 is positioned above the second electrical coil 112. The first electrical coil may be referred to herein as the "main coil." The second electrical coil may be referred to herein as the "secondary coil."

The second electrical coil 112 is connected through the sensor circuit 114 to the data processor 116. When the signal is applied to the first electrical coil 110, the voltage appearing on the second electrical coil 112 is measured by the sensor circuit 114. Both the current passing through the first electrical coil 110 and the voltage induced in the second electrical coil 112 are synchronously detected with the synchronous detector. Real and imaginary parts of the current for the first electrical coil 110 and the voltage of the second electrical coil 112 are measured. The data processor 116 uses the current detected in the first electrical coil 110 to determine the resistivity of the sample and the distance from the lower surface of the sample to the first electrical coil 110.

The data processor 116 may display the resistivity using the display device, or may compare the resistivity to an expected resistivity based on the metal or sample that the user selected from the database. In this case, the display device may display an indication of validity. For example, if the measured resistivity falls within a predetermined error range of the expected resistivity, the display device may indicate that the resistivity matches the expected resistivity. The display device may indicate a percent deviation from the expected resistivity. If the measured resistivity does not fall within the predetermined error range of the expected resistivity, the display device may indicate that the sample is likely fake or altered.

The data processor 116 uses the measured voltage induced in the second electrical coil 112 by the voltage applied to the first electrical coil 110 to determine a quantity referred to herein as "electrical thickness." The data processor 116 compares the electrical thickness to the physical thickness of the sample as part of the validation process.

A sine wave voltage generated by the signal generator 102 is applied to the second electrical coil 112, and the current passing through the second electrical coil 112 is measured by the third sensor circuit 120. The data processor 116 determines the distance from the upper surface of the sample to the second electrical coil 112 based on the measured current passing through the second electrical coil 112. The data processor then determines the thickness of the sample based on the determined distance from the lower surface of the sample to the first electrical coil 110, the determined distance from the upper surface of the sample to the second electrical coil 112, and the known distance between the first electrical coil 110 and the second electrical coil 112.

The display device may display the thickness, and may indicate the expected dimensions of the sample, such as length, width, or diameter. The user can use the scale shown on the device platform to check whether the sample has the expected dimensions. According to some embodiments, the user uses the display device and the input device to enter the measured dimensions. The data processor 116 calculates the specific gravity and reports the resistivity, specific gravity, and weight of the sample, and shows in a simple way on the display device whether the sample meets the criteria of a valid PM sample.

Figure 5:
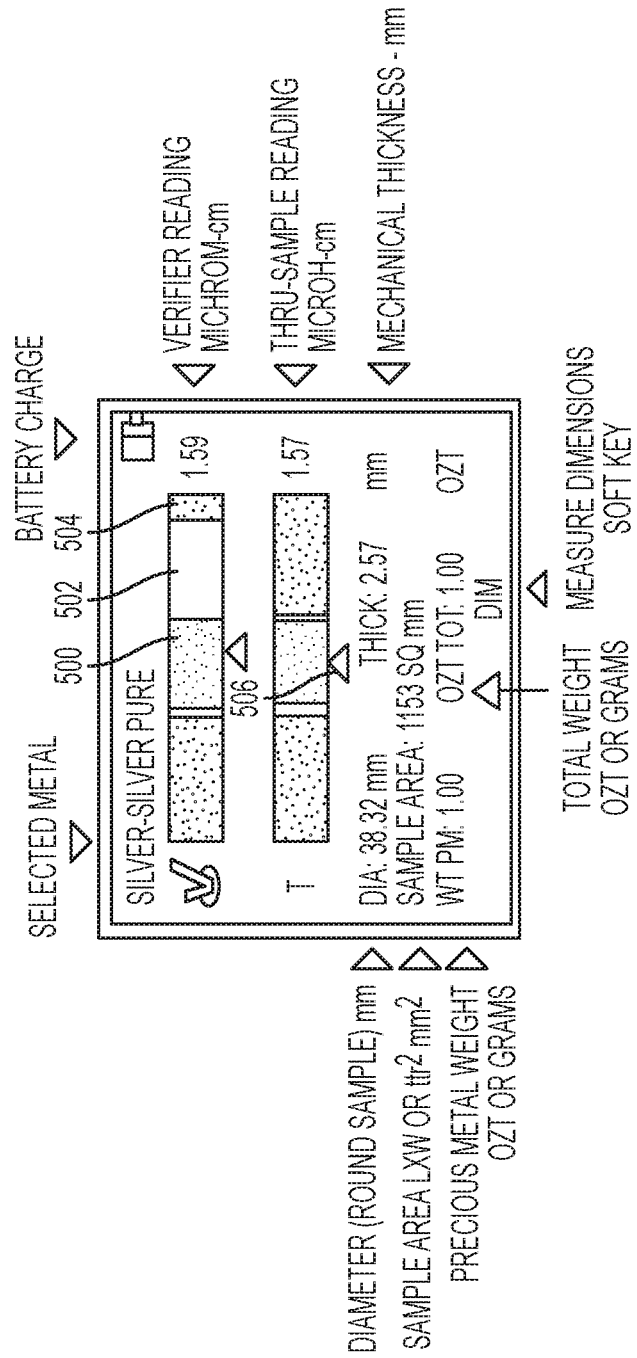
FIG. 5 shows the an example display according to some embodiments.

According to some embodiments of the invention, the display provides numeric and non-numeric information for validating the sample. For example, as shown in FIG. 5, the output display may provide an expected range of values for the surface electrical property, referred to as the "Verifier Reading" in FIG. 5. A green region 500 may indicate an expected range of values for a particular sample. A yellow region 502 on either side of the green region may indicate values that are not optimal, but may be acceptable, depending on whether the other measurements for the sample fall within acceptable ranges. A red region 504 on either side of the yellow region indicates values that are not acceptable. If the sample reading falls within the red region 504, the sample is likely fake or altered.

The display may provide similar green, yellow, and red regions for the bulk electrical property, referred to in FIG. 5 as the "Thru-Sample Reading." An arrow 506 indicates where the measured value for the sample falls within the green, yellow, and red regions. In FIG. 5, the measured value for the surface and bulk electrical properties fall within the green regions. The display may also show a numerical value for the surface and bulk electrical properties. The display may also show one or more of a diameter, an area, a thickness, a precious metal weight, and a total weight of the sample. The thickness may be measured by the device using the methods described herein. The display may also show the expected metal, which may be selected by the user prior to performing measurements on the sample. The display may also indicate the amount of charge remaining in the device's battery.

Validation Process

The first electrical coil 110 and the signal generator 102 in combination with the sensor system 108 and data processor 116 measure the resistivity of the surface of the sample and the distance from first electrical coil 110 to the lower surface of the sample. These components in combination with the second electrical coil 112 are used to find a frequency at which the current through the first electrical coil 110 and the voltage induced in the second electrical coil 112 have a predetermined phase difference. According to some embodiments, this phase difference is 45 degrees, though the embodiments of the invention are not limited to this value. The frequency at which the phase difference is 45 degrees is proportional to the metal resistivity divided by the "electrical thickness," a quantity that is discussed in more detail below.

The second electrical coil 112 in combination with the third sensor circuit 120 and the data processor 116 measures the distance from the second electrical coil 112 to the upper surface of the sample. The data processor 116 uses the two measured distances to calculate the thickness, or height, of the sample. The distance between the first electrical coil 110 and the second electrical coil 112 is known, so the thickness of the sample=distance between coils−distance from first electrical coil 110−distance from second electrical coil 112. This value is referred to herein as the "mechanical thickness" or the "thickness value."

The data processor uses the measured value of the current through the first electrical coil 110 to determine the resistivity of the sample. The algorithm for computing the resistivity is described in more detail below.

The data processor 116 divides the determined resistivity by the frequency at which the current through the first electrical coil 110 and the voltage induced in the second electrical coil 112 have the predetermined phase difference. This quotient is referred to herein as "electrical thickness." In this way, the mechanical thickness and electrical thickness are determined. In order for the sample to have the correct resistivity through its bulk, the electrical thickness must equal the mechanical thickness.

A built-in weight scale or a separate weight scale is used to measure the weight of the sample. The data processor 116 uses the measured weight in combination with the mechanical thickness to determine the area of the sample, which is either $\pi \times radius^2$ in the case of a round coin or length×width in the case of the rectangular bar. Virtually all PM samples are in one of these two forms, and the radius, length and width are easy to measure by conventional means. Note that the weight scale can be used or not at the discretion of the user, where the user can enter the known total weight, or the PM weight, instead of having it measured. In some cases it is not easy to measure the weight of a sample, for example, when it is mounted in a hard plastic case. According to some embodiments, the detection system does not include a weight sensor, since most users already have a scale and can easily enter the weight.

According to some embodiments, the user measures the diameter in the case of a coin, or the length and width in the case of a bar, using the scale provided on the upper surface of the device, or by measurement with another measurement device such as a pair of calipers, for example. The user then enters this information using the user interface. The data processor 116 uses the dimensions entered, in combination with the mechanical thickness and the weight, to calculate the specific gravity. The data processor may display the resistivity, the weight, the specific gravity, and the thickness, on the display device. These values all must agree with those of the expected metal element or alloy. If they do not agree, then the PM sample is altered or fake.

The sample target indicates to the user where to place the sample to be tested. The input device in combination with the display device allows the user to enter the coin type, the bar type, or the metal alloy, and the database contains the specific gravity and resistivity of the metal. These values are used in the calculation of the specific gravity and the electrical thickness of the sample.

The data processor 116 determines the authenticity of the sample using the algorithms described here and displays an indication of the authenticity of the sample using the display device. The PM sample is only valid if 1) the electrical thickness equals the mechanical thickness, 2) the resistivity of the sample metal agrees with that of the selected metal or alloy, and 3) the weight in combination with the volume calculates to the correct specific gravity.

How to Make the System

According to some embodiments of the invention, a circuit board holds and connects the data processor 116, the sensor system 108 including an analog-to-digital converter and a synchronous detector, the input device, the display device, the AC power supply, and a memory containing a program for execution and a metal database. The circuit board holds or connects to the weight sensor (if included), the first electrical coil 110, and the second electrical coil 112. The display device and input device are conveniently placed for the user on the housing, as is the target area. The synchronous detector can be a hardware detector, or performed in software or in a field-programmable gate array as multipliers.

According to some embodiments, the detection system is connected to an external weight scale and reads the weight from that scale.

A length scale can be included on the detection system, for example, as part of the housing or printed in a convenient place. Alternatively, the user can measure the dimensions of the sample with calipers or a ruler. Alternatively, an electronic method for measuring distance can be built-in, for example a wire with a capstan could deploy a measuring wire to measure the sample's diameter or length and width.

The data processor according to some embodiments is a microprocessor. The microprocessor may be a PC or tablet, connected by a conventional interface such as USB or Bluetooth, and also have the keypad and display. According to some embodiments, the housing includes the measurement components but not the display device or input device. In this case, all the inputs and displays can be done by a conventional computer or pad.

The first electrical coil 110 and second electrical coil 112 can be essentially the same and their functions can be interchanged. Also, other measurement modes can be used. For example, the resistivity of the surface of the sample can be measured for a quick check, and the user can control whether the complete measurement, such as thickness and specific gravity, is performed. If the surface resistivity is wrong, the other measurements are unnecessary to determine if the sample is altered or fake, and therefore the verification process may be terminated.

The system according to some embodiments may include two or more pairs of coils. FIGS. 4A and 4B shows an example that includes two pairs of coils. In FIG. 4A, upper coil 418 and its corresponding lower coil (not shown) have a larger area than upper coil 420 and its corresponding pair (no shown). The pair of smaller coils may be spaced closer together than the pair of larger coils, as shown in FIG. 4A. The larger coils may be used to examine samples that are thicker or have a larger surface area. The smaller coils may be used to examine thinner samples, or samples with a smaller surface area. Each pair may connect to the sensor system such that the measurements described herein may be performed using either pair of electrical coils. An LED 422 may indicate that the larger pair of electrical coils is in use, while a second LED 424 may indicate that the smaller pair of electrical coils is in use. The user may select the appropriate pair of electrical coils for a given sample using the user interface. The system will then perform measurements on the sample using the selected pair of electrical coils.

Using the Detection System

Described herein is an example in which a user tests the validity of a 1 oz. gold coil using the detection system. The user selects pure gold from the database, and the data processor retrieves the specific gravity for pure gold, 19.4 grams per CC, and the resistivity for pure gold, 2.2 micro Ohm cm.

The system uses the built-in scale to weigh the sample, and it weighs 31.14 grams. Alternatively, an external scale is used to weigh to sample, and the weight is communicated to the data processor directly from the external scale, for example using a wired or wireless communication system, or the user inputs the weight using the input device. The detection system then determines the resistivity of the bottom surface of the sample, which in this example is 2.2 micro Ohm Cm. Thus, the sample's resistivity matches the resistivity for pure gold that was pulled from the database.

The detection system determines the mechanical thickness using the bottom and top coils to measure the distance to the top and bottom surfaces, respectively, and subtracting the distance between the coils. The data processor determines that the mechanical thickness is 2.62 mm. Then the system measures the electrical thickness by a generating low frequency voltage at the bottom coil reading the voltage at the top coil, and adjusting the sine frequency until the phase angle between the current in the lower coil and the voltage in the upper coil is 45 degrees. Using this frequency, it calculates the electrical thickness, and gets 2.62 mm. The terms "lower coil" and "upper coil" may refer to the first electrical coil and second electrical coil, respectively, or to the second electrical coil and first electrical coil, respectively. The roles of the first and second electrical coils are interchangeable, and are independent of the orientation (i.e., above or below) of one electrical coil with respect to the other electrical coil. Further, the two coils are not required to be stacked vertically, but could assume alternative orientations as long as the two coils are opposite one another and separated by a distance.

Using the weight and the mechanical thickness, and the database value for specific gravity, the user is advised of the expected diameter of the coin, 30.0 mm. The user moves the coin to the measuring scale and reads the diameter, which is 30.0 mm. Alternatively, the user interface my indicate the expected diameter on the display screen, as described above, and the user may place the coin on the surface of the device to compare the coin's diameter to the expected diameter.

In this way the surface resistivity, the bulk resistivity, the thickness and diameter, and the specific gravity are all checked and must agree with the gold values from the metal database. The agreement doesn't have to be perfect. Typically agreement within 5% for resistivity, agreement within 5% between electrical and mechanical thickness, and agreement within 7% for diameter are sufficient to prove that the coin is valid, or in this example, that it is made from pure gold. The user interface may indicate a % error, and may also non-numerically indicate whether the % error for a given sample is acceptable.

If the "pure gold" coin were in fact made from tungsten which has been gold plated, then the surface resistivity would be wrong. The weight, thickness, diameter, and specific gravity could all be in agreement with the expected values, but the lack of agreement of the surface resistivity would enable the detection system to determine that the sample is not valid.

If the "pure gold" coin were made from a copper alloy that has the same resistivity as gold, then the surface resistivity would be in agreement with the resistivity retrieved from the metal database, and the mechanical and electrical thicknesses would also agree. However, the specific gravity would not match the specific gravity stored in the metal database, and the data processor would determine that the sample was invalid.

If the "pure gold" coin were made from heavily gold clad tungsten, then the surface resistivity may match the value in the metal database, and the weight and specific gravity could be as expected. However, the mechanical and electrical thickness would not be equal because the piece of tungsten in the middle of the coin would have the wrong resistance, and the electrical thickness would not agree with the mechanical thickness. Thus, the data processor would determine that the sample was not a pure gold coin.

For all precious metals and their alloys, one of the conditions described above would fail to be met if the material were altered or fake.

The embodiments of the invention are not limited to ascertaining the validity of a precious metal sample. The system and methods could be used to test other metals and alloys for their correct composition, or to identify the metal or alloy.

Measurement Procedure

A typical measurement procedure according to some embodiments of the invention is described below. While the steps are described in a particular order, the embodiments of the invention are not limited to this order. One skilled in the art will appreciate how the steps can be performed in an alternative order to gather the necessary information for the data processor to make a determination of validity. Further, the materials and values described below are purely exemplary and are intended to elucidate the system and methods described herein in a non-limiting manner.

According to some embodiments, the user begins the measurement process by entering information about the sample using the input device. The sample information may include a metal type or coin type, for example, "22 k gold," or "Krugerrand." The user may also enter the expected weight ($W_e$) of the sample.

The data processor then retrieves information from the metal database based on the information provided by the user. According to some embodiments, the data processor extracts the following values from the metal database: specific gravity ($G_e$), resistance ($R_e$), and thickness ($T_e$) if a specific coin or bar is selected. The subscript "e" is used herein to indicate that these are expected values, as opposed to values based on measurements of the sample. Temperature coefficients, resistance range, and other minor adjustments can also be retrieved from the metal database.

Figure 8:
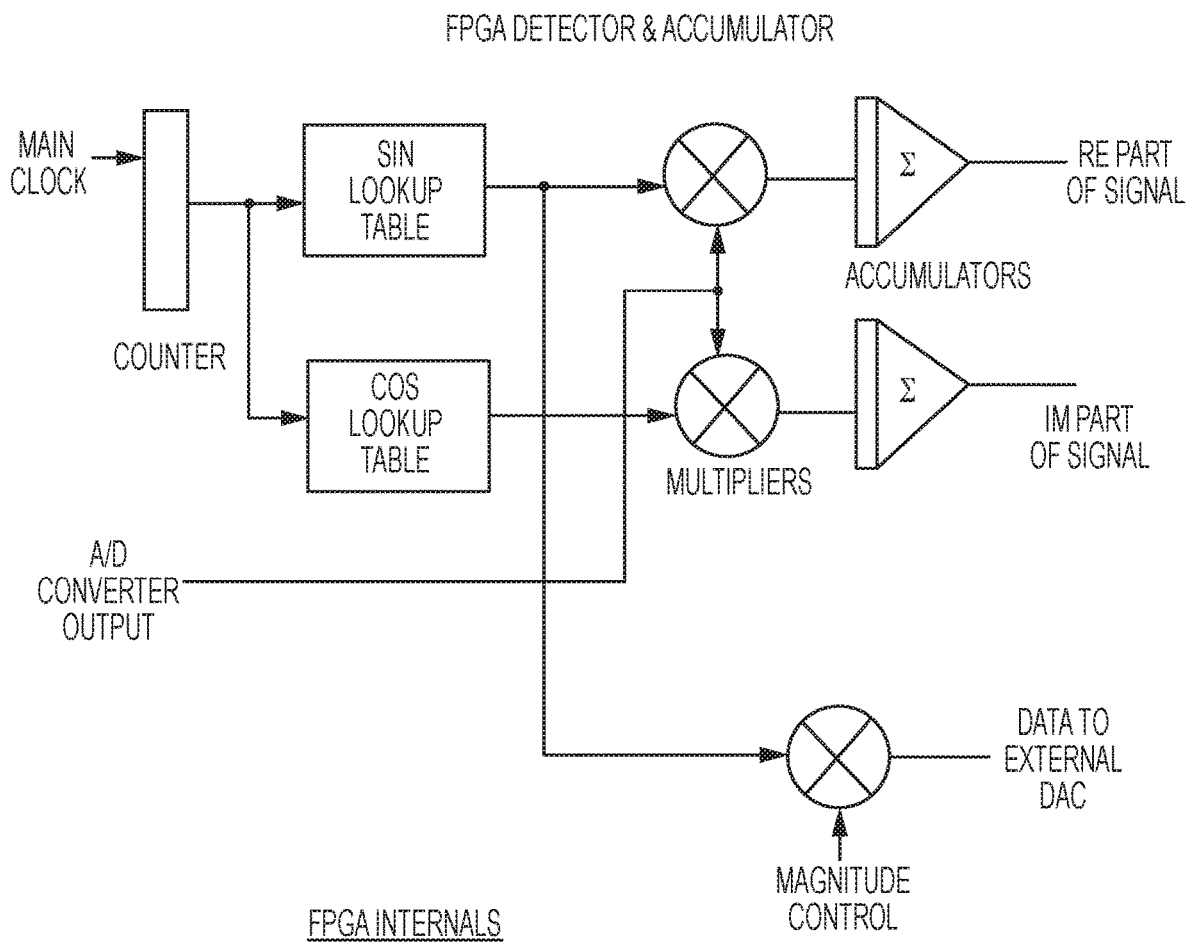
FIG. 8 shows the internals of the field-programmable gate array (FPGA), and how the phase angles are measured off the analog/digital signals according to some embodiments.

The system then calibrates the first and second electrical coils. This is done without a sample placed between the coils. The data processor applies a voltage to the first electrical coil using the AC power supply, and the sensor system measures the real Re and imaginary Im parts of the current $I_{1c}$ passing through the first electrical coil. FIG. 8 illustrates the structure of a field-programmable gate array (FPGA) according to some embodiments that is used to measure the real and imaginary parts of detected signals. The data processor uses the real and imaginary parts of the current to calculate the calibration inductance Lie and the calibration resistance $R_{1c}$ of the first electrical coil at frequency f:

$$L_{1c} = 1/(2\,Pi\,f\,Im(I_{1c})) \tag{1}$$

$$R_{1c} = 1/Re(I_{1c}) \tag{2}$$

This process also occurs for the second electrical coil, giving $L_{2c}$ and $R_{2c}$.

The data processor then instructs the user to place the sample on the target area between the first electrical coil and the second electrical coil. The data processor applies a voltage to the first electrical coil using the AC power supply, and the sensor system measures the real Re and imaginary Im parts of the current $I_{1s}$ passing through the first electrical coil when the sample is present. The system then calculates the inductance $L_{1s}$ and resistance $R_{1s}$ of the first electrical coil when the sample is present:

$$L_{1s}=1/(2\, Pi\, f\, Im(I_{1s})) \qquad (3)$$

$$R_{1s}=1/Re(I_{1s}) \qquad (4)$$

The data processor then uses the calibration inductance $L_{1c}$ and resistance $R_{1c}$ and the sample inductance $L_{1s}$ and resistance $R_{1s}$ to calculate two values referred to herein as "Q" and "k" for first electrical coil:

$$k_1 = 1 - L_{s1}/L_{c1} \qquad (5)$$

$$Q_1 = (L_{c1} - L_{s1})/(R_{c1} - R_{s1}) \qquad (6)$$

The data processor then calculates the sample resistance $r_s$:

$$r_s = \alpha Q_1\,\hat{}\,2 \qquad (7)$$

where $\alpha$ is a constant based on the sensor and the frequency.

The data processor also calculates the distance Dis from the first electrical coil to the sample:

$$D_{1s} = \text{function}(k_1) \qquad (8)$$

where the function is a Pade or other curve fit to a measured relationship between k and $D_{1s}$.

In order to calculate the distance $D_{2s}$ from the second electrical coil to the sample, the data processor applies a voltage to the second electrical coil when the sample is present using the AC power supply, and the sensor system measures the real Re and imaginary Im parts of the current $I_{2s}$ passing through the second electrical coil when the sample is present. The data processor then calculates the inductance $L_{2s}$ of the second electrical coil when the sample is present using equation (3), and calculates $k_2$ using equation (5). The distance $D_{2s}$ from the second electrical coil to the sample is determined to be $$D_{2s} = \text{function}(k_2) \qquad (9)$$

where the function is a Pade or other curve fit to a measured relationship between $k_2$ and $D_{2s}$.

Figure 9:
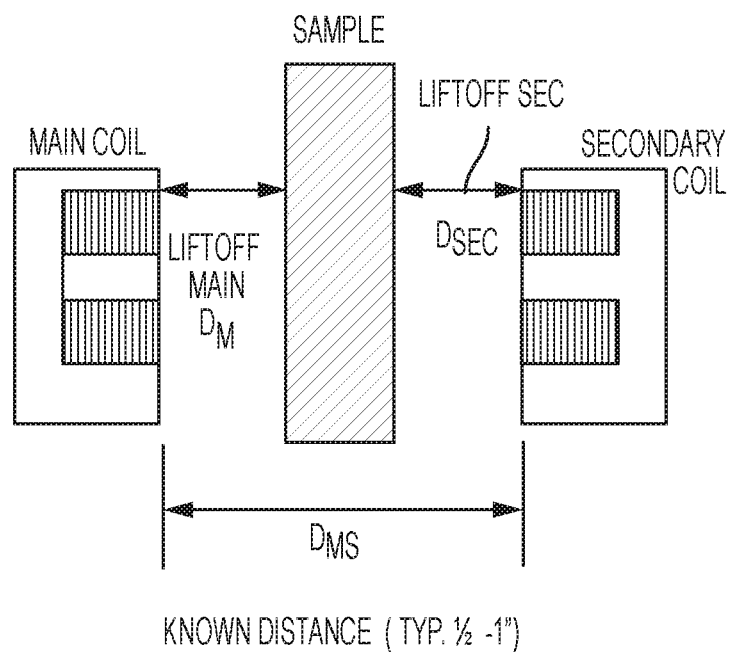
FIG. 9 shows schematically how the mechanical thickness of the sample is measured according to some embodiments.

The data processor then calculates the mechanical thickness $T_m$ of the sample:

$$T_m = D_{12} - D_{1s} - D_{2s} \qquad (10)$$

where $D_{12}$ is the distance between the first electrical coil and the second electrical coil. The process is illustrated schematically in FIG. 9. Alternatively, the data processor may receive a value for the mechanical thickness. For example, the user may measure the thickness and enter the thickness value using a user interface. The data processor may use the received thickness value for the calculations below instead of performing the steps outlined above to calculate the thickness.

The system then obtains the weight $W_s$ of the sample, either using a built-in or external yet integrated weight sensor (for example, one that is wired or wirelessly connected to the system), or prompts the user to enter the weight of the sample if the system does not have an integrated scale.

Figure 10:
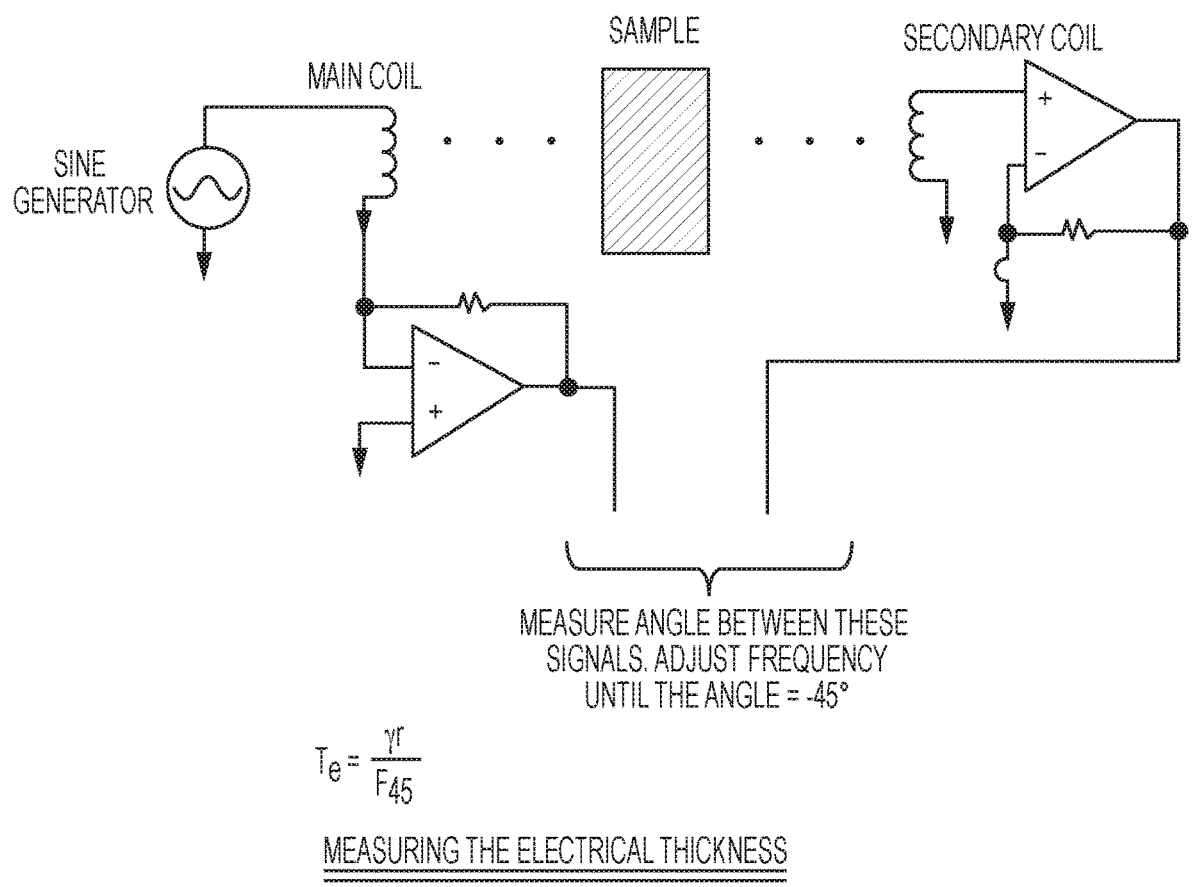
FIG. 10 shows how the electrical thickness is measured according to some embodiments.

Next, the system measures the electrical thickness $T_e$ of the sample. FIG. 10 illustrates schematically the system and process for measuring the electrical thickness according to some embodiments. The data processor uses the AC power supply to drive the first electrical coil. The sensor system measures the current in the first electrical coil and the voltage induced in the second electrical coil. The sensor system reads the phase angle $\varphi$ between the current $I_{1s}$ in the first electrical coil and the voltage $V_{2s}$ in the second electrical coil when the sample is present:

$$\varphi = \tan^{-1}\frac{\text{Im}(I_{1S})}{\text{Re}(I_{1S})} - \tan^{-1}\frac{\text{Im}(V_{2S})}{\text{Re}(V_{2S})} \qquad (11)$$

The data processor instructs the AC power supply to adjust the frequency of the voltage applied to the first electrical coil until $\varphi$ has a predetermined value, for example, −45 degrees. This can be done by an iterative search procedure using Newton's method, or by other methods. This is a hardware measurement; the frequency is adjusted until the correct frequency is generated. The frequency at which $\varphi$ becomes −45 degrees is $F_{45}$.

The thickness is a function of $r_s$ and $F_{45}$. The resistance $r_s$ was obtained using equation (7). The electrical thickness $T_e$ is calculated as $$T_e = \gamma r_s / F_{45} \qquad (12)$$

where $\gamma$ is a constant for the sensor, adjusted slightly for any distance $D_{1s}$ corrections that are necessary. The electrical thickness $T_e$ can be calculated based on $F_{45}$ using equation (12), and reported to the user as a numerical value and/or as an arrow indicating a position in a range of expected values, as shown in FIG. 5. Alternatively or additionally, the device may calculate a frequency for which $\varphi$ is expected to be −45 degrees. The sensor system may apply this frequency and measure the angle $\varphi$. The arctangent of $\varphi$ should be 1 if the frequency $F_{45}$ is exactly as expected (arctan (45 degrees)=1). The device may display the bulk measurement result to the user as a % error in this angle arctangent. For example, arctan (43.5 degrees)=0.95, so this represents a 5% error in the expected frequency. The display may show green, yellow, and red regions of the bulk reading to correspond to certain % error in this frequency. This method only requires one bulk frequency measurement to get a result, as opposed to performing multiple measurements to determine $F_{45}$.

Next, the data processor calculates the area $A_s$ of the sample based on the mechanical thickness $T_m$, the weight $W_s$, and the specific gravity $G_s$ retrieved from the metal database:

$$A_s = W_s / (G_s T_m) \qquad (13)$$

If the sample is a coin, the data processor calculates the expected radius:

$$\text{Radius} = (\text{Area}/\pi)\,\hat{}\,(\tfrac{1}{2}) \qquad (14)$$

If the user selected a metal type and not a coin, then the user measures the radius or length and width of the sample, and the data processor determines whether the radius or length and width measured by the user agrees with the area calculated based on the weight $W_s$, specific gravity $G_s$, and mechanical thickness $T_m$.

Finally, the data processor generates a report to the user that is displayed using the display device. The following criteria must be met for the sample to be authentic:

1) The sample resistance $r_s$ must match the value $r_e$ in the metal database for the coin or bullion (typically within +−3%).

2) The mechanical thickness $T_m$ must match the electrical thickness $T_e$ ($T_m=T_e$ typically within +−5%).
3) The weight $W_s$ must match the expected weight $W_e$ for the coin or bullion (typically within +−0.1%).
4) The mechanical thickness $T_m$ must agree with that of the selected coin or bullion, or the measured dimensions must match the calculated area (either the π×diameter or the length×width, typically within 5%).

If these criteria are met, the sample must be the metal, alloy, or coin selected, and the display device indicates that the sample is authentic. If any of the criteria are not met, then the display device indicates that the sample is not authentic. The display device may also display the expected and calculated values related to the criteria, and may indicate which criteria are or are not met.

From the perspective of the user, the procedure is actually simple. The user enters the coin, bullion, or metal type, and the expected weight of either the precious metal or the entire sample (for example, a Krugerrand has 31.11 grams of gold, but weighs 33.93 grams). The user hits a start button, places the sample on the target area, and then the results are displayed on the display device. Readings that are outside the expected range may be displayed in red, marginal ones in yellow, and readings within the expected range in green. This way, at a glance, the user can see whether the sample is valid.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

I claim:

1. A system for verifying authenticity of precious metal coins and bars, comprising:
    a sensor system defining a sample region configured to receive a precious metal coin or a precious metal bar therein, said sensor system comprising:
        a first electrical coil;
        a second electrical coil spaced apart from said first electrical coil with said sample region therebetween; and
        an adjustable support configured to separate said first electrical coil from said second electrical coil by a distance that can be adjusted by a user;
    a sample support arranged to support said precious metal coin or said precious metal bar in said sample region;
    a data processor configured to communicate with said sensor system so as to receive a detection signal therefrom and to provide an output signal;
    a data storage device configured to communicate with said data processor, said data storage device configured to store at least some physical properties corresponding to a precious metal of interest; and
    an output display configured to communicate with said data processor to receive said output signal and to display information based on said output signal,
    wherein said sensor system is configured to detect a bulk electrical property of said precious metal coin or said precious metal bar, said bulk electrical property being a property measured from a first surface of said precious metal coin or said precious metal bar to a second surface of said precious metal coin or said precious metal bar opposing said first surface,
    wherein said data processor is configured to process said detection signal from said sensor system and to retrieve a stored physical property corresponding to a precious metal from said data storage device to provide said output signal such that said output signal includes a measured value of said bulk electrical property and a corresponding range of expected values of said bulk electrical property, and
    wherein said output display uses said output signal to display information based on said measured value of said bulk electrical property and said corresponding range of expected values of said bulk electrical property for said user to be able to make an authenticity verification of said precious metal coin or said precious metal bar.

2. The system for verifying authenticity of precious metal coins and bars according to claim 1, further comprising:
    a signal generator,
    wherein said sensor system further comprises:
        a sensor circuit selectively connecting said signal generator to said first and second electrical coils, said sensor circuit being configured to provide a measurement of a current in said first electrical coil and a measurement of a voltage induced in said second electrical coil, and
    wherein said data processor is configured to process said measurement of said current in said first electrical coil and said measurement of said voltage induced in said second electrical coil and to retrieve said stored physical property corresponding to said precious metal from said data storage device to provide said output signal such that said output signal includes said measured value of said bulk electrical property and said corresponding range of expected values of said bulk electrical property.

3. The system for verifying authenticity of precious metal coins and bars according to claim 2, wherein said data processor is configured to provide said output signal based on a phase shift between said measurement of said current and said measurement of said voltage.

4. The system for verifying authenticity of precious metal coins and bars according to claim 2, wherein said bulk electrical property is a bulk resistivity of said precious metal coin or said precious metal bar.

5. The system for verifying authenticity of precious metal coins and bars according to claim 2, wherein said data processor is configured to control said signal generator to adjust a frequency of a voltage applied to said first electrical coil such that a phase shift between said measurement of said current and said measurement of said voltage has a predetermined value; and
    wherein said data processor is configured to provide said output signal based on said frequency at which said phase shift has said predetermined value.

6. The system for verifying authenticity of precious metal coins and bars according to according to claim 1, further comprising:
    a signal generator,
    wherein said sensor system further comprises:
        a sensor circuit selectively connecting said signal generator to said first electrical coil to provide a measurement of a current in said first electrical coil,
    wherein said data processor is configured to process said measurement of said current in said first electrical coil and to retrieve a stored physical property corresponding to a precious metal from said data storage device to provide said output signal such that said output signal includes a measured value of a surface electrical property and a corresponding range of expected values of said surface electrical property, and wherein said output display is configured to use said output signal to display information based on said measured value of said surface electrical property and said corresponding range of expected values of said surface electrical property for said user to be able to make an authenticity verification of said precious metal coin or said precious metal bar.

7. The system for verifying authenticity of precious metal coins and bars according to claim 6, wherein said sensor system further comprises a third sensor circuit selectively connecting said signal generator to said second electrical coil to provide a measurement of a current in said second electrical coil, wherein said data processor is configured to process said measurement of said current in said second electrical coil to provide said output signal such that said output signal includes a measured value of a thickness value of said precious metal coin or said precious metal bar.

8. The system for verifying authenticity of precious metal coins and bars according to claim 7, wherein said adjustable support further comprises an encoder in communication with said data processor, said encoder being configured to provide a measurement of a distance between said first electrical coil and said second electrical coil to said data processor, wherein said data processor is further configured to process said measurement of said distance to provide said output signal such that said output signal includes said measured value of said thickness value of said precious metal coin or said precious metal bar.

9. The system for verifying authenticity of precious metal coins and bars according to claim 1, further comprising:

a signal generator, wherein said sensor system further comprises:

a first sensor circuit selectively connecting said signal generator to said first electrical coil, said first sensor circuit being configured to provide a measurement of a current in said first electrical coil, and a second sensor circuit selectively connecting said signal generator to said second electrical coil, said second sensor circuit being configured to provide a measurement of a current in said second electrical coil; and wherein said data processor is configured to process said measurement of said current in said first electrical coil and said measurement of said current in said second electrical coil to provide said output signal such that said output signal includes at least a measured value of a thickness value of said precious metal coin or said precious metal bar, and wherein said output display is configured to use said output signal to display information based on said thickness value of said precious metal coin or said precious metal bar for said user to be able to make an authenticity verification of said precious metal coin or said precious metal bar.

10. The system for verifying authenticity of precious metal coins and bars according to claim 9, wherein said data processor is further configured to retrieve a specific gravity value corresponding to a precious metal from said data storage device and receive a weight value corresponding to said precious metal coin or said precious metal bar, and to provide said output signal such that said output signal further includes an expected diameter of said precious metal coin or an expected area of said precious metal bar.

11. The system for verifying authenticity of precious metal coins and bars according to claim 10, wherein said adjustable support further comprises an encoder in communication with said data processor, said encoder being configured to provide a measurement of a distance between said first electrical coil and said second electrical coil to said data processor, wherein said data processor is further configured to:

process said measurement of said current through said first electrical coil to determine a first distance between said first electrical coil and said precious metal coin or said precious metal bar;

process said measurement of said current through said second electrical coil to determine a second distance between said second electrical coil and said precious metal coin or said precious metal bar; and provide said output signal such that said output signal includes at least said measured value of said thickness value of said precious metal coin or said precious metal bar based on said first distance, said second distance, and said distance provided by said encoder.

12. The system for verifying authenticity of precious metal coins and bars according to claim 11, wherein said data processor is configured to calculate an expected area of said precious metal coin or said precious metal bar based on said thickness value, said specific gravity value, and said weight value, and wherein said output display provides a non-numerical indication of said expected area and an acceptable error range to allow said user to compare said expected area to an actual area of said precious metal coin or said precious metal bar.

13. The system for verifying authenticity of precious metal coins and bars according to claim 1, wherein said adjustable support further comprises an encoder in communication with said data processor, said encoder being configured to provide a measurement of a distance between said first electrical coil and said second electrical coil to said data processor.

14. The system for verifying authenticity of precious metal coins and bars according to claim 1, further comprising a user input system configured to communicate with said data storage device and said data processor, wherein said user input system allows said user to select at least one of a precious metal type, alloy parameters, weight, or shape.

15. The system for verifying authenticity of precious metal coins and bars according to claim 1, further comprising a weight measurement component in communication with said data processor.

16. A system for verifying authenticity of precious metal coins and bars according to claim 15, wherein said data processor is configured to receive a weight value of said precious metal coin or said precious metal bar from said weight measurement component.

17. A system for verifying authenticity of precious metal coins and bars, comprising:

a sensor system defining a sample region configured to receive a precious metal coin or a precious metal bar therein, said sensor system comprising:

a first electrical coil;

a second electrical coil spaced apart from said first electrical coil by a first distance with said sample region therebetween;
a third electrical coil;
a fourth electrical coil spaced apart from said third electrical coil by a second distance with said sample region therebetween, said second distance being different from said first distance;
a sample support arranged to support said precious metal coin or said precious metal bar in said sample region;
a user input system configured to allow a user to select said first and second electrical coils or said third and fourth electrical coils;
a data processor configured to communicate with said sensor system and said user input system so as to receive a detection signal detected by said first and second electrical coils or said third and fourth electrical coils based on said user's selection, and to provide an output signal;
a data storage device configured to communicate with said data processor, said data storage device configured to store at least some physical properties corresponding to a precious metal of interest; and
an output display configured to communicate with said data processor to receive said output signal and to display information based on said output signal,
wherein said sensor system is configured to detect a bulk electrical property of said precious metal coin or said precious metal bar, said bulk electrical property being a property measured from a first surface of said precious metal coin or said precious metal bar to a second surface of said precious metal coin or said precious metal bar opposing said first surface,
wherein said data processor is configured to process said detection signal from said sensor system and to retrieve a stored physical property corresponding to a precious metal from said data storage device to provide said output signal such that said output signal includes a measured value of said bulk electrical property and a corresponding range of expected values of said bulk electrical property, and
wherein said output display uses said output signal to display information based on said measured value of said bulk electrical property and said corresponding range of expected values of said bulk electrical property for said user to be able to make an authenticity verification of said precious metal coin or said precious metal bar.

18. A method for verifying authenticity of precious metal coins and bars using an electronic apparatus, comprising:
inputting into said electronic apparatus information identifying at least a type of a precious metal coin or a precious metal bar to be verified;
selecting a distance between a pair of electrical coils included in said electronic apparatus, said pair of electrical coils being configured to receive a precious metal coin or said precious metal bar therebetween;
performing a measurement of a bulk electrical property of said precious metal coin or said precious metal bar using said pair of electrical coils spaced apart by said selected distance, said bulk electrical property being a property measured from a first surface of said precious metal coin or said precious metal bar to a second surface of said precious metal coin or said precious metal bar opposing said first surface;
retrieving a stored bulk electrical property of said precious metal coin or said precious metal bar corresponding to said measured bulk electrical property for said inputted type of said precious metal coin or said precious metal bar; and
providing information from said electronic apparatus for verification of authenticity of said precious metal coin or said precious metal bar based on said measured bulk electrical property and said retrieved bulk electrical property.

19. The method for verifying authenticity of precious metal coins and bars using an electronic apparatus according to claim 18, wherein selecting said distance between said pair of electrical coils comprises adjusting a distance between said pair of electrical coils using an adjustable support.

20. The method for verifying authenticity of precious metal coins and bars using an electronic apparatus according to claim 18, wherein said electronic apparatus comprises a first electrical coil and a second electrical coil spaced apart from said first electrical coil by a first distance, a third electrical coil, and a fourth electrical coil spaced apart from said third electrical coil by a second distance, said second distance being different from said first distance, and
wherein selecting said distance between said pair of electrical coils comprises selecting said first and second electrical coils or said third and fourth electrical coils.

* * * * *